(12) United States Patent
Mihan et al.

(10) Patent No.: US 7,629,464 B2
(45) Date of Patent: Dec. 8, 2009

(54) MONOCYCLOPENTADIENYL COMPLEXES

(75) Inventors: Shahram Mihan, Bad Soden (DE); Markus Enders, Heidelberg (DE); Pablo Fernandez, Dublin (IE)

(73) Assignee: Basell Polyolefine GmbH, Wesseling (DE)

( * ) Notice: Subject to any disclaimer, the term of this patent is extended or adjusted under 35 U.S.C. 154(b) by 74 days.

(21) Appl. No.: 10/583,575

(22) PCT Filed: Dec. 15, 2004

(86) PCT No.: PCT/EP2004/014253

§ 371 (c)(1), (2), (4) Date: May 7, 2007

(87) PCT Pub. No.: WO2005/058983

PCT Pub. Date: Jun. 30, 2005

(65) Prior Publication Data

US 2007/0213483 A1 Sep. 13, 2007

Related U.S. Application Data

(60) Provisional application No. 60/543,447, filed on Feb. 10, 2004.

(30) Foreign Application Priority Data

Dec. 19, 2003  (DE) .............................. 103 60 059

(51) Int. Cl.
*C07F 17/00* (2006.01)
*B01J 31/00* (2006.01)

(52) U.S. Cl. .......................... 546/4; 526/126; 526/161; 526/943; 502/103; 502/120

(58) Field of Classification Search ................. 502/103, 502/120; 526/126, 161, 943; 546/4
See application file for complete search history.

(56) References Cited

U.S. PATENT DOCUMENTS

| | | | |
|---|---|---|---|
| 3,242,150 A | 3/1966 | Scoggin | |
| 3,248,179 A | 4/1966 | Norwood | |
| 3,709,853 A | 1/1973 | Karapinka | |
| 4,015,059 A | 3/1977 | Karol | |
| 5,532,396 A | 7/1996 | Winter et al. | |
| 5,576,260 A | 11/1996 | Winter et al. | |
| 5,612,428 A | 3/1997 | Winter et al. | |
| 5,808,122 A | 9/1998 | Herrmann et al. | |
| 6,255,418 B1 | 7/2001 | Jolly et al. | |
| 6,417,302 B1 | 7/2002 | Bohnen | |
| 6,437,161 B1 | 8/2002 | Mihan et al. | |
| 6,589,905 B1 | 7/2003 | Fischer et al. | |
| 6,699,948 B2 | 3/2004 | Mihan et al. | |
| 6,756,505 B1 | 6/2004 | Kristen et al. | |
| 6,784,261 B1 | 8/2004 | Schopf et al. | |
| 6,787,498 B2 | 9/2004 | Mihan et al. | |
| 6,812,185 B2 | 11/2004 | Fischer et al. | |
| 6,838,563 B2 | 1/2005 | Mihan et al. | |
| 6,919,412 B1 | 7/2005 | Mihan et al. | |
| 2003/0036658 A1 | 2/2003 | Mihan et al. | |
| 2003/0036662 A1 | 2/2003 | Mihan et al. | |
| 2003/0055267 A1 | 3/2003 | Mihan et al. | |
| 2003/0236164 A1 | 12/2003 | Fischer et al. | |
| 2004/0214970 A1 | 10/2004 | Schopf et al. | |
| 2004/0242880 A1* | 12/2004 | Mihan et al. | .................. 546/2 |
| 2007/0213205 A1* | 9/2007 | Mihan | .................. 502/113 |
| 2007/0213483 A1* | 9/2007 | Mihan et al. | .................. 526/126 |
| 2007/0213484 A1* | 9/2007 | Mihan et al. | .................. 526/160 |
| 2007/0255033 A1* | 11/2007 | Kipke et al. | .................. 526/352 |
| 2008/0064838 A1* | 3/2008 | Mihan et al. | .................. 526/204 |
| 2008/0097053 A1* | 4/2008 | Mihan et al. | .................. 526/126 |

FOREIGN PATENT DOCUMENTS

| | | |
|---|---|---|
| DE | 19630580 | 2/1998 |
| DE | 19716015 | 10/1998 |
| EP | 659757 | 6/1995 |
| EP | 742046 | 11/1996 |
| EP | 1212333 | 6/2002 |
| JP | 11 199621 | 7/1999 |
| WO | 91/09882 | 7/1991 |
| WO | 96/00243 | 1/1996 |
| WO | 96/13529 | 5/1996 |
| WO | 97/04015 | 2/1997 |
| WO | 97/36937 | 10/1997 |
| WO | 98/22486 | 5/1998 |
| WO | 98/27124 | 6/1998 |
| WO | 98/40419 | 9/1998 |
| WO | 99/06414 | 2/1999 |
| WO | 00/05277 | 2/2000 |
| WO | 00/24787 | 5/2000 |

(Continued)

OTHER PUBLICATIONS

Kirk-Othmer, "Olefin Polymers (High Pressure Polyethylene); High Pressure (Low and Intermediate Density) Polyethylene;" *Encyclopedia of Chemical Technology*, vol. 16, p. 402-420 (1981).

M. Enders et al., "8-Quinolylcyclopentadienyl, a Ligand with a Tailored Fit for Chelate Complexes," *Chem. Ber.*, vol. 129, p. 459-463 (1996).

(Continued)

*Primary Examiner*—Porfirio Nazario Gonzalez
(74) *Attorney, Agent, or Firm*—Jarrod N. Raphael

(57) ABSTRACT

Monocyclopentadienyl complexes in which the cyclopentadienyl system is substituted by at least one bridged donor, where the bridge contains at least one atom of group 14 of the Periodic Table and at least one atom of group 15 or 16 of the Periodic Table, and a catalyst system comprising at least one of the monocyclopentadienyl complexes, and also methods of preparing them, the use of the catalyst system for the polymerization or copolymerization of olefins and a process for preparing polyolefins by polymerization or copolymerization of olefins in the presence of the catalyst system and the preparation of the associated cyclopentadienyl system.

6 Claims, No Drawings

FOREIGN PATENT DOCUMENTS

| WO | 00/31090 | 6/2000 |
|---|---|---|
| WO | 00/35928 | 6/2000 |
| WO | 01/09148 | 2/2001 |
| WO | 01/12641 | 2/2001 |
| WO | 01/41920 | 6/2001 |
| WO | 01/92346 | 12/2001 |

OTHER PUBLICATIONS

R. Halterman, "Synthesis and Applications of Chiral Cyclopentadienylmetal Complexes," *Chem. Rev.*, vol. 92(5), p. 965-994 (1992).

S. Strauss, "The Search for Larger and More Weakly Coordinating Anions," *Chem. Rev.*, vol. 93(3), p. 927-942 (1993).

V. Gibson et al., "Novel olefin polymerization catalysts based on iron and cobalt," *Chem. Commun.*, p. 849-850 (1998).

M. Brookhart et al., "Highly Active Iron and Cobalt Catalysts for the Polymerization of Ethylene," *J. Am. Chem. Soc.*, vol. 120(16), p. 4049-4050 (1998).

H. Brinzinger et al., "*ansa*-Metallocene derivatives—XVII. Racemic and *meso* diastereomers of group IV metallocene derivatives with symmetrically substituted, dimethylsilanediyl-bridged ligand frameworks. crystal structure of R,S-Me$_2$Si(3-t-Bu-5-MeC$_5$H$_2$)$_2$ZrCl$_2$;" *Jouranl of Organometallic Chemistry*, vol. 369, p. 359-370 (1989).

P. Jutzi et al., "Cyclopentadienyl compounds with nitrogen donors in the side-chain," *Journal of Organometallic Chemistry 500*, p. 175-185 (1995).

L. Fieser & M. Fieser, Chapter 33, "Heterocyclen," *Lehrbuch der Organischen Chemie*, 3$^{rd}$ revised edition, Verlag Chemie, Weinheim (1957).

J. Ewen et al., "Expanding the Scope of Metallocene Catalysis: Beyond Indenyl and Fluorenyl Derivatives," *Springer Verlag*, p. 150-169 (1999).

*Chemical Reviews*, vol. 100(4), p. 1167-1681 (2000).

A. Döhring et al., "Donor-Ligand-Substituted Cyclopentadienyl-chromium(III) Complexes: A New Class of Alkene Polymerization Catalyst. 1. Amino-Substituted Systems," *Organometallics*, vol. 19(4), p. 388-402 (2000).

G. Jiménez et al., "Cyclopentadienyl-Amido Ligands with a Pendant "-NHR" Amino Functionality in Titanium Chemistry. Molecular Structure of [Ti{η$^5$-C$_5$H$_4$SiMe$_2$-η-N(CH$_2$)$_2$-η-NHCHME$_2$}Cl$_2$]," *Organometallics*, vol. 21(11), p. 2189-2195 (2002).

\* cited by examiner

MONOCYCLOPENTADIENYL COMPLEXES

The present invention relates to monocyclopentadienyl complexes in which the cyclopentadienyl system is substituted by at least one bridged donor, where the bridge contains at least one atom of group 14 of the Periodic Table and at least one atom of group 15 or 16 of the Periodic Table, and to a catalyst system comprising at least one of the monocyclopentadienyl complexes, and also to methods of preparing them.

In addition, the invention relates to the use of the catalyst system for the polymerization or copolymerization of olefins and to a process for preparing polyolefins by polymerization or copolymerization of olefins in the presence of the catalyst system and to polymers obtainable therewith.

Many of the catalysts which are used for the polymerization of α-olefins are based on immobilized chromium oxides (cf., for example, Kirk-Othmer, "Encyclopedia of Chemical Technology", 1981, vol. 16, p. 402). These generally give ethylene homopolymers and copolymers having high molecular weights, but are relatively insensitive to hydrogen and thus do not allow the molecular weight to be controlled in a simple manner. In contrast, the use of bis(cyclopentadienyl)chromium (U.S. Pat. No. 3,709,853), bis(indenyl)chromium or bis(fluorenyl)chromium (U.S. Pat. No. 4,015,059) applied to an inorganic, oxidic support allows the molecular weight of polyethylene to be controlled in a simple manner by addition of hydrogen.

As in the case of Ziegler-Natta systems, catalyst systems having a uniquely defined, active center, known as single-site catalysts, have recently been sought in the case of the chromium compounds, too. Targeted variation of the ligand framework should enable activity, copolymerization behavior of the catalyst and the properties of polymers obtained in this way to be altered in a simple manner.

DE 197 10615 describes monocyclopentadienylchromium compounds substituted by donor ligands by means of which ethene and also propene can be polymerized. Here, the donor is from group 15 and is uncharged. The donor is bound to the cyclopentadienyl ring via a $(ZR_2)_n$ fragment, where R is hydrogen, alkyl or aryl, Z is an atom of group 14 and n is $\geq 1$. DE 196 30 580 specifically claims Z=carbon in combination with an amine donor.

WO 96/13529 describes reduced transition metal complexes of groups 4 to 6 of the Periodic Table with polydentate monoanionic ligands. These include cyclopentadienyl ligands containing a donor function. The examples are restricted to titanium compounds.

WO 01/12641 describes monocyclopentadienyl complexes of chromium, molybdenum and tungsten which bear, in particular, quinolyl or pyridyl donors which are bound either directly or via a $C_1$ or Si bridge to the cyclopentadienyl system.

WO 01/92346 discloses cylopentadienyl complexes of groups 4-6 of the Periodic Table of the Elements in which a dihydrocarbyl-Y group, where Y is an element of group 14 of the Periodic Table of the Elements, which bears particular Lewis bases is bound to the cyclopentadienyl system.

The activities of the abovementioned catalyst systems are not yet optimized. In addition, the polymers and copolymers formed usually have a very high molecular weight.

It is an object of the invention to discover further transition metal complexes based on cyclopentadienyl ligands having a bridged donor which are suitable for the polymerization of olefins and can be prepared in a simple manner and in high yields.

We have found that this object is achieved by monocyclopentadienyl complexes comprising the structural feature of the formula $Cp\text{-}(Z\text{-}A)_m M^4$ (I), where the variables have the following meanings:
Cp is a cyclopentadienyl system,
A is an uncharged donor containing at least one atom of group 15 or 16 of the Periodic Table,
Z is a bridge between A and Cp containing at least one atom of group 14 of the Periodic Table and at least one atom of group 15 or 16 of the Periodic Table,
$M^4$ is titanium, zirconium, hafnium, vanadium, niobium, tantalum, chromium, molybdenum or tungsten or an element of group 3 of the Periodic Table and the lanthanides and
m is 1, 2 or 3.

Furthermore, we have found a catalyst system comprising the monocyclopentadienyl complexes of the present invention, the use of the monocyclopentadienyl complexes or of the catalyst system for the polymerization or copolymerization of olefins and a process for preparing polyolefins by polymerization or copolymerization of olefins in the presence of the monocyclopentadienyl complex or of the catalyst system and polymers obtainable in this way. In addition, a process and intermediates in this process have been found.

The monocyclopentadienyl complexes of the invention comprise the structural element of the formula $Cp\text{-}(Z\text{-}A)_m M^4$ (I), where the variables are as defined above. Further ligands can therefore be bound to the metal atom $M^4$. The number of further ligands depends, for example, on the oxidation state of the metal atom. Possible further ligands do not include further cyclopentadienyl systems. Suitable further ligands are monoanionic and dianionic ligands as are described, for example, for X. In addition, Lewis bases such as amines, ethers, ketones, aldehydes, esters, sulfides or phosphines can be bound to the metal center M. The monocyclopentadienyl complexes can be monomeric, dimeric or oligomeric. The monocyclopentadienyl complexes are preferably in monomeric form.

$M^4$ is a metal selected from the group consisting of titanium, zirconium, hafnium, vanadium, niobium, tantalum, chromium, molybdenum and tungsten. The oxidation state of the transition metals $M^4$ in catalytically active complexes is usually known to those skilled in the art. Chromium, molybdenum and tungsten are very probably present in the oxidation state +3, titanium, zirconium, hafnium and vanadium in the oxidation state 4, with titanium and vanadium also being able to be present in the oxidation state 3. However, it is also possible to use complexes whose oxidation state does not correspond to that of the active catalyst. Such complexes can then be appropriately reduced or oxidized by means of suitable activators. $M^4$ is preferably titanium, vanadium, chromium, molybdenum or tungsten. Particular preference is given to chromium in the oxidation states 2, 3 and 4, in particular 3.

m can be 1, 2 or 3, i.e. 1, 2 or 3 groups -Z-A can be bound to Cp, and when 2 or 3 Y groups are present, these can be identical or different. Preference is given to only one group -Z-A being bound to Cp (m=1).

The uncharged donor A is an uncharged functional group containing an element of group 15 or 16 of the Periodic Table or a carbene, e.g. amine, imine, carboxamide, carboxylic ester, ketone (oxo), ether, thioketone, phosphine, phosphite, phosphine oxide, sulfonyl, sulfonamide, carbenes such as N-substituted imidazol-2-ylidene or unsubstituted, substituted or fused, partially unsaturated heterocyclic or heteroaromatic ring systems. The donor A can be intermolecularly or intramolecularly bound to the transition metal $M^4$ or not be bound to the transition metal. The donor A is preferably bound intramolecularly to the metal center $M^A$. Particular preference is given to monocyclopentadienyl complexes comprising the structural element of the formula Cp-Z-A-$M^A$.

Z is a bridge between A and Cp containing at least one atom of group 14 of the Periodic Table, in particular carbon or silicon and at least one atom of group 15 or 16 of the Periodic Table, in particular oxygen, sulfur, nitrogen or phosphorus. At least one atom of group 14 of the Periodic Table and at least one atom of group 15 or 16 of the Periodic Table are constituents of the direct link between A and Cp. This direct link—atom(group 14)-atom(group 15 or 16)—is a minimum constituent of Z. Z can be bound to Cp via the atom of group 14 or of group 15 or of group 16 of the Periodic Table. Z is preferably bound to Cp via the atom of group 14.

Cp is a cyclopentadienyl system which may be substituted as desired and/or fused with one or more aromatic, aliphatic, heterocyclic or heteroaromatic rings, with 1, 2 or 3 substituents, preferably 1 substituent, being formed by the group -Z-A and/or 1, 2 or 3 substituents, preferably 1 substituent, being substituted by the group -Z-A and/or the aromatic, aliphatic, heterocylic or heteroaromatic fused ring bearing 1, 2 or 3 substituents -Z-A, preferably 1 substituent -Z-A. The cyclopentadienyl skeleton itself is a $C_5$ ring system having 6π electrons, where one of the carbon atoms can also be replaced by nitrogen or phosphorus, preferably phosphorus. Preference is given to using $C_5$ ring systems in which none of the carbon atoms is replaced by a heteroatom. This cyclopentadienyl skeleton can, for example, have a heteroaromatic containing at least one atom from the group consisting of N, P, O and S or an aromatic fused onto it. Here, "fused on" means that the heterocycle and the cyclopentadienyl skeleton share two atoms, preferably carbon atoms. The cyclopentadienyl system is bound to $M^A$.

Particularly useful monocyclopentadienyl complexes have the formula Cp-Z-A-$M^A$ (II), where the variables have the following meanings:
Cp-Z-A is

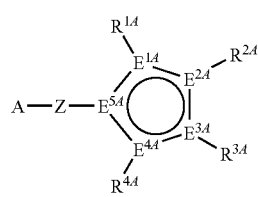

(III)

where the variables have the following meanings:
$E^{1A}$-$E^{5A}$ are each carbon or not more than one $E^{1A}$ to $E^{5A}$ is phosphorus,
$R^{1A}$-$R^{4A}$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl part and 6-20 carbon atoms in the aryl part, $NR^{5A}_2$, $N(SiR^{5A}_3)_2$, $OR^{5A}$, $OSiR^{5A}_3$, $SiR^{5A}_3$, $BR^{5A}_2$, where the organic radicals $R^{1A}$-$R^{4A}$ may also be substituted by halogens and two vicinal radicals $R^{1A}$-$R^{4A}$ may also be joined to form a five-, six- or seven-membered ring, and/or two vicinal radicals $R^{1A}$-$R^{4A}$ are joined to form a five-, six- or seven-membered heterocycle containing at least one atom from the group consisting of N, P, O and S,
the radicals $R^{5A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part and two geminal radicals $R^{5A}$ may also be joined to form a five- or six-membered ring, Z is a divalent bridge between A and Cp and is selected from the group consisting of

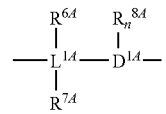

where
$L^{1A}$ is carbon, silicon or germanium, in particular silicon,
$D^{1A}$ is an atom of group 15 or 16 of the Periodic Table, in particular oxygen, sulfur, nitrogen or phosphorus,
n is 0 when $D^{1A}$ is an atom of group 16 and is 1 when $D^{1A}$ is an atom of group 15,
$R^{6A}$-$R^{8A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{9A}_3$, where the organic radicals $R^{6A}$-$R^{8A}$ may also be substituted by halogens and two geminal or vicinal radicals $R^{6A}$-$R^{8A}$ may also be joined to form a five- or six-membered ring and
the radicals $R^{9A}$ are each, independently of one another, hydrogen, $C_1$-$C_{20}$-alkyl, $C_2$-$C_{20}$-alkenyl, $C_6$-$C_{20}$-aryl or arylalkyl having from 1 to 10 carbon atoms in the alkyl part and 6-20 carbon atoms in the aryl part, $C_1$-$C_{10}$-alkoxy or $C_6$-$C_{10}$-aryloxy and two radicals $R^{9A}$ may also be joined to form a five- or six-membered ring, and
A is an uncharged donor group containing one or more atoms of group 15 and/or 16 of the Periodic Table of the Elements or a carbene, preferably an unsubstituted, substituted or fused, heteroaromatic ring system, and
$M^A$ is a metal selected from the group consisting of titanium in the oxidation state 3, vanadium, chromium, molybdenum and tungsten.

In preferred cyclopentadienyl systems Cp, all $E^{1A}$ to $E^{5A}$ are carbon.

The polymerization behavior of the metal complexes can likewise be influenced by variation of the substituents $R^{1A}$-$R^{4A}$. The number and type of the substituents can influence the ability of the olefins to be polymerized to gain access to the metal atom $M^A$. This makes it possible to modify the activity and selectivity of the catalyst in respect of various monomers, in particular bulky monomers. Since the substituents can also influence the rate of termination reactions of the growing polymer chain, the molecular weight of the polymers formed can also be altered in this way. The chemical structure of the substituents $R^{1A}$ to $R^{4A}$ can therefore be varied within a wide range in order to achieve the desired results and obtain a tailored catalyst system. Possible carboorganic substituents $R^{1A}$-$R^{4A}$ are, for example, the following: hydrogen, $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_1$-$C_{10}$-alkyl group and/or $C_6$-$C_{10}$-aryl group as substituent, e.g. cylopropyl, cyclobutyl, cyclopentyl, cyclohexyl, cycloheptyl, cyclooctyl, cyclononyl or cyclododecyl, $C_2$-$C_{22}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may be substituted by further alkyl groups, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl which may be substituted by further alkyl groups, e.g. benzyl, o-, m-, p-methylbenzyl, 1- or 2-ethylphenyl, where two of the radicals $R^{1A}$ to $R^{4A}$ may also be joined to form a 5-, 6- or 7-membered ring and/or two vicinal radicals $R^{1A}$-$R^{4A}$ may be joined to form a five-, six- or seven-membered heterocycle containing at least one atom from the group consisting of N, P, O and S and/or the organic radicals $R^{1A}$-$R^{4A}$ may also be substituted by halogens such as fluorine, chlorine or bromine. Furthermore, $R^{1A}$-$R^{4A}$ can be amino $NR^{5A}{}_2$ or $N(SiR^{5A}{}_3)_2$, alkoxy or aryloxy $OR^{5A}$, for example dimethylamino, N-pyrrolidinyl, picolinyl, methoxy, ethoxy or isopropoxy. In organosilicon substituents $SiR^{5A}{}_3$, the radicals $R^{5A}$ may be the same carboorganic radicals as described in more detail above for $R^{1A}$-$R^{4A}$, with two radicals $R^{5A}$ also being able to be joined to form a 5- or 6-membered ring, e.g. trimethylsilyl, triethylsilyl, butyldimethylsilyl, tri-tert-butylsilyl, triallylsilyl, triphenylsilyl or dimethylphenylsilyl. These $SiR^{5A}{}_3$ radicals can also be bound to the cyclopentadienyl skeleton via an oxygen or nitrogen, for example trimethylsilyloxy, triethylsilyloxy, butyldimethylsilyloxy, tributylsilyloxy or tri-tert-butylsilyloxy. Preferred radicals $R^{1A}$-$R^{4A}$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl- or ortho-dichloro-substituted phenyls, trialkyl- or trichloro-substituted phenyls, naphthyl, biphenyl and anthranyl. As organosilicon substituents, particular preference is given to trialkylsilyl groups having from 1 to 10 carbon atoms in the alkyl radical, in particular trimethylsilyl groups.

Two vicinal radicals $R^{1A}$-$R^{4A}$ together with the atoms $E^{1A}$-$E^{5A}$ bearing them may form a heterocycle, preferably a heteroaromatic, containing at least one atom from the group consisting of nitrogen, phosphorus, oxygen and sulfur, particularly preferably nitrogen and sulfur, with the atoms $E^{1A}$-$E^{5A}$ in the heterocycle or heteroaromatic preferably being carbon. Preference is given to heterocycles and heteroaromatics having a ring size of 5 or 6 ring atoms. Examples of 5-membered heterocycles which may contain from one to four nitrogen atoms and/or a sulfur or oxygen atom as ring atoms in addition to carbon atoms are 1,2-dihydrofuran, furan, thiophene, pyrrole, isoxazole, 3-isothiazole, pyrazole, oxazole, thiazole, imidazole, 1,2,4-oxadiazole, 1,2,5-oxadiazole, 1,3,4-oxadiazole, 1,2,3-triazole or 1,2,4-triazole. Examples of 6-membered heteroaryl groups which may contain from one to four nitrogen atoms and/or a phosphorus atom are pyridine, phosphabenzene, pyridazine, pyrimidine, pyrazine, 1,3,5-triazine, 1,2,4-triazine or 1,2,3-triazine. The 5-membered and 6-membered heterocycles may also be substituted by $C_1$-$C_{10}$-alkyl, $C_6$-$C_{10}$-aryl, arylalkyl having from 1 to 10 carbon atoms in the alkyl part and 6-10 carbon atoms in the aryl part, trialkylsilyl or halogens such as fluorine, chlorine or bromine, dialkylamide, alkylarylamide, diarylamide, alkoxy or aryloxy or be fused with one or more aromatics or heteroaromatics. Examples of benzo-fused 5-membered heteroaryl groups are indole, indazole, benzofuran, benzothiophene, benzothiazole, benzoxazole and benzimidazole. Examples of benzo-fused 6-membered heteroaryl groups are chromane, benzopyran, quinoline, isoquinoline, cinnoline, phthalazine, quinazoline, quinoxaline, 1,10-phenanthroline and quinolizine. Naming and numbering of the heterocycles has been taken from Lettau, Chemie der Heterocyclen, 1st Edition, VEB, Weinheim 1979. The heterocycles/heteroaromatics are preferably fused to the cyclopentadienyl skeleton via a C—C double bond of the heterocycle/heteroaromatic. Heterocycles/heteroaromatics having one heteroatom are preferably 2,3- or b-fused.

Cyclopentadienyl systems Cp having a fused-on heterocycle are, for example, thiapentalene, 2-methylthiapentalene, 2-ethylthiapentalene, 2-isopropylthiapentalene, 2-n-butylthiapentalene, 2-tert-butylthiapentalene, 2-trimethylsilylthiapentalene, 2-phenylthiapentalene, 2-naphthylthiapentalene, 3-methylthiapentalene, 4-phenyl-2,6-dimethyl-1-thiapentalene, 4-phenyl-2,6-diethyl-1-thiapentalene, 4-phenyl-2,6-diisopropyl-1-thiapentalene, 4-phenyl-2,6-di-n-butyl-1-thiapentalene, 4-phenyl-2,6-di-trimethylsilyl-1-thiapentalene, azapentalene, 2-methylazapentalene, 2-ethylazapentalene, 2-isopropylazapentalene, 2-n-butylazapentalene, 2-trimethylsilylazapentalene, 2-phenylazapentalene, 2-naphthylazapentalene, 1-phenyl-2,5-dimethyl-1-azapentalene, 1-phenyl-2,5-diethyl-1-azapentalene, 1-phenyl-2,5-di-n-butyl-1-azapentalene, 1-phenyl-2,5-di-tert-butyl-1-azapentalene, 1-phenyl-2,5-di-trimethylsilyl-1-azapentalene, 1-tert-butyl-2,5-dimethyl-1-azapentalene, oxapentalene, phosphapentalene, 1-phenyl-2,5-dimethyl-1-phosphapentalene, 1-phenyl-2,5-diethyl-1-phosphapentalene, 1-phenyl-2,5-di-n-butyl-1-phosphapentalene, 1-phenyl-2,5-di-tert-butyl-1-phosphapentalene, 1-phenyl-2,5-di-trimethylsilyl-1-phosphapentalene, 1-methyl-2, 5-dimethyl-1-phosphapentalene, 1-tert-butyl-2,5-dimethyl-1-phosphapentalene, 7-cyclopenta-[1,2]thienyl[3,4]cyclopentadiene or 7-cyclopenta[1,2]pyrrolyl[3,4]cyclopentadiene.

In further, preferred cyclopentadienyl systems Cp, four of the radicals $R^{1A}$-$R^{4A}$, i.e. two pairs of two vicinal radicals together, form two heterocycles, in particular heteroaromatics. The heterocyclic systems are the same as those described in more detail above. Examples of cyclopentadienyl systems Cp having two fused-on heterocycles are 7-cyclopentadithiophene, 7-cyclopentadipyrrole and 7-cyclopentadiphosphole.

The synthesis of such cyclopentadienyl systems having a fused-on heterocycle is described, for example, in the above-mentioned WO 98/22486. In "metalorganic catalysts for synthesis and polymerization", Springer Verlag 1999, Ewen et al., p. 150 ff, describe further syntheses of the cyclopentadienyl systems.

Particularly preferred substituents $R^{1A}$-$R^{4A}$ are the carboorganic substituents described above and carboorganic substituents which form a cyclic fused ring system, i.e. together with the $E^{1A}$-$E^{5A}$ skeleton, preferably together with a $C_5$-cyclopentadienyl skeleton, form, for example, an unsubstituted or substituted indenyl, benzindenyl, phenanthrenyl or tetrahydroindenyl system.

Examples of such cyclopentadienyl systems (without the group -Z-A, which is preferably located in the 1 position) are 3-methylcyclopentadienyl, 3-ethylcyclopentadienyl, 3-isopropylcyclopentadienyl, 3-tert-butylcyclopentadienyl, dialkylcyclopentadienyl such as tetrahydroindenyl, 2,4-dimethylcyclopentadienyl or 3-methyl-5-tert-butylcyclopentadienyl, trialkylcyclopentadienyl such as 2,3,5-trimethylcyclopentadienyl or tetraalkylcyclopentadienyl such as 2,3,4,5-tetramethylcyclopentadienyl, and also indenyl, 2-methylindenyl, 2-ethylindenyl, 2-isopropylindenyl, 3-methylindenyl, benzindenyl and 2-methylbenzindenyl. The fused ring system may bear further $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part, $NR^{5A}{}_2$, $N(SiR^{5A}{}_3)_2$, $OR^{5A}$, $OSiR^{5A}{}_3$ or $SiR^{5A}{}_3$ groups, e.g. 4-methylindenyl, 4-ethylindenyl, 4-isopropylindenyl, 5-methylindenyl, 4-phenylindenyl, 5-methyl-4-phenylindenyl, 2-methyl-4-phenylindenyl or 4-naphthylindenyl.

As in the case of metallocenes, the monocyclopentadienyl complexes of the present invention can be chiral. Thus, one of the substituents $R^{1A}$-$R^{4A}$ of the cyclopentadienyl skeleton can have one or more chiral centers, or else the cyclopentadienyl system Cp itself can be enantiotopic, so that chirality is induced only when it is bound to the transition metal M (for formalisms regarding chirality in cyclopentadienyl compounds, see R. Halterman, Chem. Rev. 92, (1992), 965-994).

The bridge Z between the cyclopentadienyl system Cp and the uncharged donor A is an organic divalent bridge which preferably consists of carbon or silicon and oxygen-, sulfur-, nitrogen- or phosphorus-containing bridge members. A change in the length of the link between the cyclopentadienyl system and A can influence the activity of the catalyst. Z is preferably bound to the Cp system via $L^{1A}$.

Possible carboorganic substituents $R^{6A}$-$R^{8A}$ on the bridge Z are, for example, the following: hydrogen, $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5- or 2,6-dimethylphen-1-yl, 2,3,4-, 2,3,5-, 2,3,6-, 2, 4.5-, 2,4,6- or 3,4,5-trimethylphen-1-yl, or arylalkyl which may be substituted by further alkyl groups, e.g. benzyl, o-, m-, p-methylbenzyl, 1- or 2-ethylphenyl, where two radicals $R^{6A}$ to $R^{8A}$ may also be joined to form a 5- or 6-membered ring, for example cyclohexane, and the organic radicals $R^{6A}$-$R^{8A}$ may also be substituted by halogens such as fluorine, chlorine or bromine, for example pentafluorophenyl or bis-3,5-trifluoromethylphen-1-yl, and alkyl or aryl.

Particularly preferred substituents $R^{6A}$ to $R^{7A}$ are hydrogen, $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, or arylalkyl which may be substituted by further alkyl groups, e.g. benzyl, o-, m-, p-methylbenzyl, 1- or 2-ethylphenyl, where two radicals $R^{6A}$ to $R^{7A}$ may also be joined to form a 5- or 6-membered ring, for example cyclohexane, and the organic radicals $R^{6A}$-$R^{7A}$ may also be substituted by halogens such as fluorine, chlorine or bromine, in particular fluorine, for example pentafluorophenyl or bis-3,5-trifluoromethylphen-1-yl, and alkyl or aryl. Particularly preferred radicals $R^{6A}$ to $R^{7A}$ are hydrogen, methyl, ethyl, 1-propyl, 2-isopropyl, 1-butyl, 2-tert-butyl, benzyl, phenyl and pentafluorophenyl.

$R^{8A}$ is preferably methyl, ethyl, n-propyl, isopropyl, n-butyl, isobutyl, tert-butyl, n-pentyl, n-hexyl, n-heptyl, n-octyl, benzyl, phenyl, ortho-dialkyl or ortho-dichloro-substituted phenyls, trialkyl- or trichloro-substituted phenyls, naphthyl, biphenyl and anthranyl.

In organosilicon substituents $SiR^{9A}_3$, the radicals $R^{9A}$ can be the same radicals as described in more detail above for $R^{6A}$-$R^{8A}$, with two radicals $R^{9A}$ also being able to be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl.

Z is preferably a —$CR^{6A}R^{7A}$-$D^{1A}(R^{8A})_n$— or —$SiR^{6A}R^{7A}$-$D^{1A}(R^{8A})_n$— group, in particular —$CR^{6A}R^{7A}$—O—, —$CR^{6A}R^{7A}$—$NR^{8A}$—, —$SiR^{6A}R^{7A}$— and —$SiR^{6A}R^{7A}$—$NR^{8A}$—, in particular —$SiR^{6A}R^{7A}$—O—. The preferred embodiments of the substituents $R^{6A}$ to $R^{8A}$ described above are likewise preferred embodiments here. —$CR^{6A}R^{7A}$— is preferably a —$CHR^{6A}$—, —$CH_2$— or —$C(CH_3)_2$— group. $L^{1A}$ in -$L^{1A}R^{6A}R^{7A}$-$D^{1A}(R^{8A})_n$— can be bound to the cyclopentadienyl system or to A. $L^{1A}$ or its preferred embodiments is preferably bound to Cp.

A is an uncharged donor containing an atom of group 15 or 16 of the Periodic Table or a carbene, preferably one or more atoms selected from the group consisting of oxygen, sulfur, nitrogen and phosphorus, preferably nitrogen and phosphorus. The donor function in A can bind intermolecularly or intramolecularly to the metal $M^A$. The donor in A is preferably bound intramolecularly to M. Possible donors are uncharged functional groups containing an element of group 15 or 16 of the Periodic Table, e.g. amine, imine, carboxamide, carboxylic ester, ketone (oxo), ether, thioketone, phosphine, phosphite, phosphine oxide, sulfonyl, sulfonamide, carbenes such as N-substituted imidazol-2-ylidene or unsubstituted, substituted or fused, heterocyclic ring systems. The synthesis of the unit in which A is bound to Z and the cyclopentadienyl radical can be carried out in a manner analogous to that described in WO 00/35928.

A is preferably a group selected from among —$OR^{10A}$, —$SR^{10A}$, —$NR^{10A}R^{11A}$, —$PR^{10A}R^{11A}$, —$C$=$NR^{10A}$ and unsubstituted, substituted or fused heteroaromatic ring systems, in particular —$NR^{10A}R^{11A}$, —$C$=$NR^{10A}$ and unsubstituted, substituted or fused heteroaromatic ring systems.

$R^{10A}$ and $R^{11A}$ are each, independently of one another, hydrogen, $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5- or 2,6-dimethylphen-1-yl, 2,3,4-, 2,3,5-, 2,3,6-, 2,4,5-, 2,4,6- or 3,4,5-trimethylphen-1-yl, arylalkyl which has from 1 to 10 carbon atoms in the alkyl part and 6-20 carbon atoms in the aryl part and may be substituted by further alkyl groups, e.g. benzyl, o-, m-, p-methylbenzyl, 1- or 2-ethylphenyl, or $SiR^{12A}_3$, where the organic radicals $R^{10A}$-$R^{11A}$ may also be substituted by halogens such as fluorine, chlorine or bromine or nitrogen-containing groups and further $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{12A}_3$ and two vicinal radicals $R^{10A}$-$R^{11A}$ may also be joined to form a five- or six-membered ring and the radicals $R^{12A}$ are each, independently of one another, hydrogen, $C_1$-$C_{20}$-alkyl, $C_2$-$C_{20}$-alkenyl, $C_6$-$C_{20}$-aryl or arylalkyl having from 1 to 10 carbon atoms in the alkyl part and 6-20 carbon atoms in the aryl part and two radicals $R^{12A}$ may also be joined to form a five- or six-membered ring.

$NR^{10A}R^{11A}$ is an amide substituent. It is preferably a secondary amide such as dimethylamide, N-ethylmethylamide, diethylamide, N-methylpropylamide, N-methylisopropylamide, N-ethylisopropylamide, dipropylamide, diisopropylamide, N-methylbutylamide, N-ethylbutylamide, N-methyl-tert-butylamide, N-tert-butylisopropylamide, dibutylamide, di-sec-butylamide, diisobutylamide, tert-amyl-tert-butylamide, dipentylamide, N-methylhexylamide, dihexylamide, tert-amyl-tert-octylamide, dioctylamide, bis(2-ethylhexyl) amide, didecylamide, N-methyloctadecylamide, N-methylcyclohexylamide, N-ethylcyclohexylamide, N-isopropylcyclohexylamide, N-tert-butylcyclohexylamide, dicyclohexylamide, pyrrolidine, piperidine, hexamethylenimine, decahydroquinoline, diphenylamine, N-methylanilide or N-ethylanilide.

In the imino group $-C=NR^{10A}$, $R^{10A}$ is preferably a $C_6-C_{20}$-aryl which may be substituted by further alkyl groups, e.g. phenyl, naphthyl, biphenyl, anthranyl, o-, m-, p-methylphenyl, 2,3-, 2,4-, 2,5- or 2,6-dimethylphen-1-yl, 2,3,4-, 2,3,5-, 2,3,6-, 2,4,5-, 2,4,6- or 3,4,5-trimethylphen-1-yl.

A is preferably an unsubstituted, substituted or fused heteroaromatic ring system whose ring can contain, in addition to carbon atoms, heteroatoms selected from the group consisting of oxygen, sulfur, nitrogen and phosphorus. Examples of 5-membered heteroaryl groups, which can contain from one to four nitrogen atoms or from one to three nitrogen atoms and/or a sulfur or oxygen atom as ring atoms in addition to carbon, are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl and 1,2,4-triazol-3-yl. Examples of 6-membered heteroaryl groups, which can contain from one to four nitrogen atoms and/or a phosphorus atom, are 2-pyridinyl, 2-phosphabenzenyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 5-membered and 6-membered heteroaryl groups can also be substituted by $C_1-C_{10}$-alkyl, $C_6-C_{10}$-aryl, arylalkyl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Naming and numbering of the heterocycles has been taken from L. Fieser and M. Fieser, Lehrbuch der organischen Chemie, 3rd revised edition, Verlag Chemie, Weinheim 1957.

Among these heteroaromatic systems A, particular preference is given to unsubstituted, substituted and/or fused six-membered heteroaromatics having 1, 2, 3, 4 or 5 nitrogen atoms in the heteroaromatic unit, in particular substituted and unsubstituted 2-pyridyl or 2-quinolyl.

A is therefore preferably a group of the formula (IV)

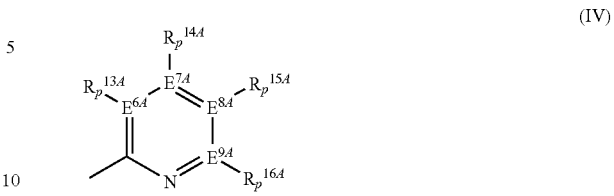

(IV)

where
$E^{6A}-E^{9A}$ are each, independently of one another, carbon or nitrogen,
$R^{13A}-R^{16A}$ are each, independently of one another, hydrogen, $C_1-C_{20}$-alkyl, $C_2-C_{20}$-alkenyl, $C_6-C_{20}$-aryl, arylalkyl having from 1 to 10 carbon atoms in the alkyl-part and 6-20 carbon atoms in the aryl part or $SiR^{17A}_3$, where the organic radicals $R^{13A}-R^{16A}$ may also be substituted by halogens or nitrogen and further $C_1-C_{20}$-alkyl, $C_2-C_{20}$-alkenyl, $C_6-C_{20}$-aryl, arylalkyl having from 1 to 10 carbon atoms in the alkyl part and 6-20 carbon atoms in the aryl part or $SiR^{17A}_3$ groups and two vicinal radicals $R^{13A}-R^{16A}$ or $R^{13A}$ and Z may also be joined to form a five- or six-membered ring and
the radicals $R^{17A}$ are each, independently of one another, hydrogen, $C_1-C_{20}$-alkyl, $C_2-C_{20}$-alkenyl, $C_6-C_{20}$-aryl or arylalkyl having from 1 to 10 carbon atoms in the alkyl part and 6-20 carbon atoms in the aryl part and two radicals $R^{17A}$ may also be joined to form a five- or six-membered ring and
p is 0 when $E^{6A}-E^{9A}$ is nitrogen and is 1 when $E^{6A}-E^{9A}$ is carbon.

In particular, 0 or 1 $E^{6A}-E^{9A}$ is nitrogen and the others are carbon. A is particularly preferably 2-pyridyl, 6-methyl-2-pyridyl, 4-methyl-2-pyridyl, 5-methyl-2-pyridyl, 5-ethyl-2-pyridyl, 4,6-dimethyl-2-pyridyl, 3-pyridazyl, 4-pyrimidyl, 6-methyl-4-pyrimidyl, 2-pyrazinyl, 6-methyl-2-pyrazinyl, 5-methyl-2-pyrazinyl, 3-methyl-2-pyrazinyl, 3-ethylpyrazinyl, 3,5,6-trimethyl-2-pyrazinyl, 2-quinolyl, 4-methyl-2-quinolyl, 6-methyl-2-quinolyl, 7-methyl-2-quinolyl, 2-quinoxalyl or 3-methyl-2-quinoxalyl.

Owing to the ease of preparation, preference is given to compounds in which Z is $-Si(CH_3)_2-O-$ or $-Si(CH_3)_2-NR^{8A}-$ and A is unsubstituted or substituted 2-quinolyl or unsubstituted or substituted 2-pyridyl. Here, A is preferably bound to $-O-$ or $-NR^{8A}-$. The preferred embodiments of the variables described above are also preferred in these preferred combinations.

$M^A$ is a metal selected from the group consisting of titanium in the oxidation state 3, vanadium, chromium, molybdenum and tungsten, preferably titanium in the oxidation state 3 and chromium. Particular preference is given to chromium in the oxidation states 2, 3 and 4, in particular 3. The metal complexes, in particular the chromium complexes, can be obtained in a simple manner by reacting the appropriate metal salts such as metal chlorides with the ligand anion (e.g. in a manner analogous to the examples in DE 197 10615).

Preference is given to monocyclopentadienyl complexes of the formula $Cp-Y_m M^A X^{1A}_n$ (V), where the variables Cp, Y, A, m and $M^A$ are as defined above and their preferred embodiments are also preferred here and
the radicals $X^{1A}$ are each, independently of one another, fluorine, chlorine, bromine, iodine, hydrogen, $C_1-C_{10}$-alkyl, $C_2-C_{10}$-alkenyl, $C_6-C_{20}$-aryl, arylalkyl having 1-10 carbon atoms in the alkyl part and 6-20 carbon atoms in the aryl part, $NR^{18A}R^{19A}$, $OR^{18A}$, $SR^{18A}$, $SO_3R^{18A}$, $OC(O)R^{18A}$, CN, SCN, β-diketonate, CO, $BF_4^-$, $PF_6^-$ or bulky noncoordinating anions or two radicals $X^{1A}$ may form a substituted or unsubstituted diene ligand, in particular a 1,3-diene ligand, and the radicals $X^{1A}$ may also be joined to one another, $R^{18A}$-$R^{19A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part, $SiR^{20A}_3$, where the organic radicals $R^{18A}$-$R^{19A}$ may also be substituted by halogens or nitrogen- and oxygen-containing groups and two radicals $R^{18A}$-$R^{19A}$ may also be joined to form a five- or six-membered ring, the radicals $R^{20A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part and two radicals $R^{20A}$ may also be joined to form a five- or six-membered ring and n is 1, 2 or 3.

The embodiments and preferred embodiments of Cp, Y, Z, A, m and $M^A$ described above also apply individually and in combination to these preferred monocyclopentadienyl complexes.

The ligands $X^{1A}$ can result, for example, from the choice of the corresponding starting metal compounds which are used for the synthesis of the monocyclopentadienyl complexes, but can also be varied afterwards. Suitable ligands $X^{1A}$ are, in particular, the halogens fluorine, chlorine, bromine or iodine, in particular chlorine. Alkyl radicals such as methyl, ethyl, propyl, butyl, vinyl, allyl, phenyl or benzyl are also advantageous ligands $X^{1A}$. Further possible ligands $X^{1A}$ are, purely by way of example and not in any way exhaustively, trifluoroacetate, $BF_4^-$, $PF_6^-$ and weakly coordinating or noncoordinating anions (cf., for example, Strauss in Chem. Rev. 1993, 93, 927-942) such as $B(C_6F_5)_4^-$.

Amides, alkoxides, sulfonates, carboxylates and β-diketonates are also particularly suitable ligands $X^{1A}$. Variation of the radicals $R^{18A}$ and $R^{19A}$ enables, for example, physical properties such as solubility to be finely adjusted. Possible carboorganic substituents $R^{18A}$-$R^{19A}$ are, for example, the following: $C_1$-$C_{20}$-alkyl which may be linear or branched, for example methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and have an internal or terminal double bond, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups and/or N- or O-containing radicals, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, 2-methoxyphenyl, 2-N,N-dimethylaminophenyl or arylalkyl which may be substituted by further alkyl groups, e.g. benzyl, o-, m-, p-methylbenzyl, 1- or 2-ethylphenyl, where $R^{18A}$ may also be joined to $R^{19A}$ to form a 5- or 6-membered ring and the organic radicals $R^{18A}$-$R^{19A}$ may also be substituted by halogens, e.g. fluorine, chlorine or bromine. In organosilicon substituents $SiR^{20A}_3$, $R^{20A}$ may be the same radicals as described in more detail above for $R^{18A}$-$R^{19A}$, with two $R^{20A}$ also being able to be joined to form a 5- or 6-membered ring. Examples of substituents $SiR^{20A}_3$ are trimethylsilyl, triethylsilyl, butyldimethylsilyl, tributylsilyl, triallylsilyl, triphenylsilyl and dimethylphenylsilyl. Preference is given to using $C_1$-$C_{10}$-alkyl such as methyl, ethyl, n-propyl, n-butyl, tert-butyl, n-pentyl, n-hexyl, n-heptyl, n-octyl and also vinyl, allyl, benzyl and phenyl as radicals $R^{18A}$ and $R^{19A}$. Some of these substituted ligands $X^{1A}$ are very particularly preferably used since they are obtainable from cheap and readily available starting materials. In a particularly preferred embodiment $X^{1A}$ is dimethylamide, methoxide, ethoxide, isopropoxide, phenoxide, naphthoxide, triflate, p-toluenesulfonate, acetate, or acetylacetonate The number n of the ligands $X^{1A}$ depends on the oxidation state of the transition metal $M^A$. The number n can therefore not be specified in general terms. The oxidation state of the transition metals $M^A$ in catalytically active complexes is usually known to a person skilled in the art. Chromium, molybdenum and tungsten are very probably present in the oxidation state +3, vanadium in the oxidation state +3 or +4. However, it is also possible to use complexes whose oxidation state does not correspond to that of the active catalyst. Such complexes can then be appropriately reduced or oxidized by means of suitable activators. Preference is given to using chromium complexes in the oxidation state +3 and titanium complexes in the oxidation state 3. Preferred monocyclopentadienyl complexes A) of this type are 1-((2-(methylamino)pyridine)dimethylsilyl)cyclopentadienylchromium(III) dichloride, 1-((2-oxy-4-methylpyridine)dimethylsilyl)cyclopentadienylchromium(III) dichloride, 1-((2-oxyquinoline)dimethylsilyl)cyclopentadienylchromium(III) dichloride, 1-((2-oxy-4-methylpyrimidine)dimethylsilyl)cyclopentadienylchromium(III) dichloride, 1-(2-oxypyridine)dimethylsilyl)cyclopentadienylchromium(III) dichloride, 1-((2-oxypyridine)dimethylsilyl)-3-methylcyclopentadienylchromium (III) dichloride, 1-((2-(methylamino)pyridine)dimethylsilyl)indenylchromium(III) dichloride, 1-((2-oxy-4-methylpyridine)dimethylsilyl)indenylchromium(III) dichloride, 1-(2-oxyquinoline)dimethylsilyl)indenylchromium(III) dichloride, 1-((2-oxy-4-methylpyrimidine)dimethylsilyl)indenylchromium(III) dichloride and 1-((2-oxypyridine)dimethylsilyl)indenylchromium(III) dichloride.

Such complexes can be synthesized by methods known per se, preferably by reacting the appropriately substituted cyclopentadienyl anions with halides of titanium, vanadium or chromium. Examples of appropriate preparative methods are described, inter alia, in Journal of Organometallic Chemistry, 369 (1989), 359-370 and in EP-A-1212333.

Furthermore, we have found a process for preparing cyclopentadiene systems of the formula (VI),

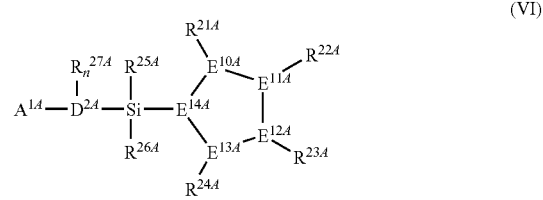

(VI)

where the variables have the following meanings:

$E^{10A}$-$E^{14A}$ are each carbon, with four adjacent $E^{10A}$-$E^{14A}$ forming a conjugated diene system and the remaining one of $E^{10A}$-$E^{14A}$ additionally bearing a hydrogen atom, $R^{21A}$-$R^{24A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part, $SiR^{28A}_3$, where the organic radicals $R^{21A}$-$R^{24A}$ may also be substituted by halogens and two vicinal radicals $R^{21A}$-$R^{24A}$ may also be joined to form a five- or six-membered ring, and/or two vicinal radicals $R^{21A}$-$R^{24A}$ are joined to form a heterocycle containing at least one atom from the group consisting of N, P, O and S, $R^{25A}$-$R^{27A}$ are each, independently of one another, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{28A}_3$, where the organic radicals $R^{25A}$-$R^{27A}$ may also be substituted by halogens and $R^{25A}$ and $R^{26A}$ and/or $R^{27A}$ and A may also be joined to form a five- or six-membered ring, the radicals $R^{28A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part and two geminal radicals $R^{28A}$ may also be joined to form a five- or six-membered ring, $A^{1A}$ is an uncharged donor group containing one or more atoms of the group 15 or 16 of the Periodic Table of the Elements or a carbene, preferably an unsubstituted, substituted or fused, heteroaromatic ring system, $D^{2A}$ is an atom of group 15 or 16 of the Periodic Table, in particular oxygen, sulfur, nitrogen or phosphorus, n is 0 when $D^{1A}$ is an atom of group 16 and is 1 when $D^{1A}$ is an atom of group 15, which comprises a) reacting a cyclopentadiene system of the formula (VII)

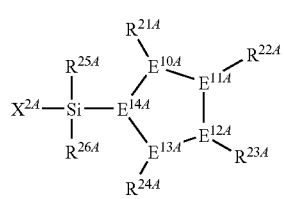

(VII)

where the additional variables have the following meanings:

$X^{2A}$ is fluorine, chlorine, bromine, iodine, $OR^{29A}$ or $SO_3R^{29A}$, $R^{29A}$ is $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{30A}_3$ and the radical $R^{29A}$ may also be substituted by halogens and the radicals $R^{30A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part and two radicals $R^{30A}$ may also be joined to form a five- or six-membered ring, with a compound $(A^{1A}$-$D^{2A}R^{27A}_n)_pX^{3A}$ where the additional variables have the following meanings:

$X^{3A}$ is hydrogen, Li, Na, K, $BeX^{4A}_o$, $MgX^{4A}_o$, $CaX^{4A}_o$, $SrX^{4A}_o$, $BaX^{4A}_o$ or $ZnX^{4A}_o$, the radicals $X^{4A}$ are each, independently of one another, fluorine, chlorine, bromine, iodine, $OR^{31A}$, $SO_3R^{31A}$, p is 1 when $X^{3A}$ is hydrogen, Li, Na or K and is 2 when o is 0, o is 0 or 1, $R^{31A}$ is $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{32A}_3$ and the radical $R^{31A}$ may also be substituted by halogens and the radicals $R^{32A}$ are each, independently of one another, hydrogen, $C_1$-$C_{20}$-alkyl, $C_2$-$C_{20}$ alkenyl, $C_6$-$C_{20}$-aryl, arylalkyl having from 1 to 10 carbon atoms in the alkyl part and 6-20 carbon atoms in the aryl part and two radicals $R^{32A}$ may also be joined to form a five- or six-membered ring.

Possible carboorganic substituents $R^{21A}$-$R^{24A}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups and/or N- or O-containing radicals, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, 2-methoxyphenyl, 2-N,N-dimethylaminophenyl, or arylalkyl which may be substituted by further alkyl groups, e.g. benzyl, o-, m-, p-methylbenzyl, 1- or 2-ethylphenyl, where two vicinal radicals $R^{21A}$-$R^{24A}$ may also be joined to form a 5- or 6-membered ring and/or two vicinal radicals $R^{21A}$-$R^{24A}$ are joined to form a heterocycle containing at least one atom from the group consisting of N, P, O and S and the organic radicals $R^{21A}$-$R^{24A}$ may also be substituted by halogens such as fluorine, chlorine or bromine. Preference is given to using hydrogen and $C_1$-$C_{10}$-alkyl such as methyl, ethyl, n-propyl, n-butyl, tert-butyl, n-pentyl, n-hexyl, n-heptyl, n-octyl, and also phenyl or benzyl as radicals $R^{21A}$ to $R^{24A}$. Particularly preferred substituents $R^{21A}$-$R^{24A}$ are also those which form a cyclic fused ring system, i.e. together with $E^{10A}$-$E^{14A}$, preferably together with a $C_5$-cyclopentadienyl skeleton, form, for example, an unsubstituted or substituted indenyl, benzindenyl, phenanthrenyl or tetrahydroindenyl system.

Possible carboorganic substituents $R^{25A}$-$R^{27A}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups and/or N- or O-containing radicals, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, 2-methoxyphenyl, 2-N,N-dimethylaminophenyl, or arylalkyl which may be substituted by further alkyl groups, e.g. benzyl, o-, m-, p-methylbenzyl, 1- or 2-ethylphenyl, where two vicinal radicals $R^{25A}$-$R^{27A}$ may also be joined to form a 5- or 6-membered ring and the organic radicals $R^{25A}$-$R^{27A}$ may also be substituted by halogens such as fluorine, chlorine or bromine. Preference is given to using $C_1$-$C_{10}$-alkyl such as methyl, ethyl, n-propyl, n-butyl, tert-butyl, n-pentyl, n-hexyl, n-heptyl, n-octyl and also phenyl or benzyl as radicals $R^{25A}$ to $R^{26A}$. Preference is given to using $C_1$-$C_{10}$-alkyl such as methyl, ethyl, n-propyl, n-butyl, tert-butyl, n-pentyl, n-hexyl, n-heptyl, n-octyl and also phenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl or benzyl as radical $R^{27A}$.

In organosilicon substituents $SiR^{28A}_3$, the radicals $R^{28A}$ can be the same radicals described in more detail above for $R^{21A}$-$R^{24A}$, where two radicals $R^{28A}$ may also be joined to form a 5- or 6-membered ring, e.g. trimethylsilyl, triethylsilyl, butyldimethylsilyl, tributylsilyl, triallylsilyl, triphenylsilyl or dimethylphenylsilyl.

$A^{1A}$ is an uncharged donor containing an atom of group 15 or 16 of the Periodic Table or a carbene, preferably one or more atoms selected from the group consisting of oxygen, sulfur, nitrogen and phosphorus, preferably nitrogen and phosphorus, e.g. amine, imine, carboxamide, carboxylic ester, ketone (oxo), ether, thioketone, phosphine, phosphite, phosphine oxide, sulfonyl, sulfonamide, carbenes such as N-substituted imidazol-2-ylidene or unsubstituted, substituted or fused, heterocyclic ring systems.

$A^{1A}$ is preferably a group selected from among $R^{28A}$—C(=O)—, $R^{28A}$—C(=$NR^{28A}$)— and unsubstituted, substituted or fused heteroaromatic ring systems which can contain heteroatoms from the group consisting of oxygen, sulfur, nitrogen and phosphorus in addition to ring carbons. Examples of 5-membered heteroaryl groups which can contain from one to four nitrogen atoms or from one to three nitrogen atoms and/or a sulfur or oxygen atom as ring members in addition to carbon atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups which can contain from one to four nitrogen atoms and/or a phosphorus atom are 2-pyridinyl, 2-phosphabenzolyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl or 1,2,4-triazin-6-yl. The 5-membered and 6-membered heteroaryl groups may also be substituted by $C_1$-$C_{10}$-alkyl, $C_6$-$C_{10}$-aryl, arylalkyl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Naming and numbering of the heterocycles has been taken from L. Fieser and M. Fieser, Lehrbuch der organischen Chemie, 3rd revised edition, Verlag Chemie, Weinheim 1957.

Among these heteroaromatic systems $A^{1A}$, particular preference is given to unsubstituted, substituted and/or fused six-membered heteroaromatics having 1, 2, 3, 4 or 5 nitrogen atoms in the heteroaromatic part, in particular substituted and unsubstituted 2-pyridyl or 2-quinolyl. $A^{1A}$ is therefore preferably a group of the formula (VII)

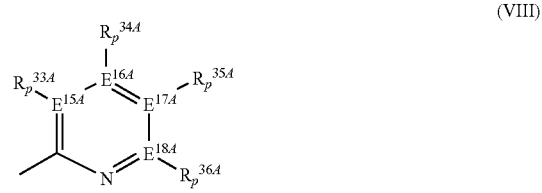

(VIII)

where
$E^{15A}$-$E^{18A}$ are each, independently of one another, carbon or nitrogen,
$R^{33A}$-$R^{36A}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{37A}_3$, where the organic radicals $R^{33A}$-$R^{36A}$ may also be substituted by halogens or nitrogen and further $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{37A}_3$ groups and two vicinal radicals $R^{33A}$-$R^{36A}$ or $R^{33A}$ and $R^{35A}$ may also be joined to form a five- or six-membered ring and
the radicals $R^{37A}$ are each, independently of one another, hydrogen, $C_1$-$C_{20}$-alkyl, $C_2$-$C_{20}$-alkenyl, $C_6$-$C_{20}$-aryl or arylalkyl having from 1 to 10 carbon atoms in the alkyl part and 6-20 carbon atoms in the aryl part and two radicals $R^{37A}$ may also be joined to form a five- or six-membered ring and
p is 0 when $E^{15A}$-$E^{18A}$ is nitrogen and is 1 when $E^{15A}$-$E^{18A}$ is carbon.

In particular, 0 or 1 $E^{15A}$-$E^{18A}$ is nitrogen and the others are carbon. $A^{1A}$ is particularly preferably 2-pyridyl, 6-methyl-2-pyridyl, 4-methyl-2-pyridyl, 5-methyl-2-pyridyl, 5-ethyl-2-pyridyl, 4,6-dimethyl-2-pyridyl, 3-pyridazyl, 4-pyrimidyl, 6-methyl-4-pyrimidyl, 2-pyrazinyl, 6-methyl-2-pyrazinyl, 5-methyl-2-pyrazinyl, 3-methyl-2-pyrazinyl, 3-ethylpyrazinyl, 3,5,6-trimethyl-2-pyrazinyl, 2-quinolyl, 4-methyl-2-quinolyl, 6-methyl-2-quinolyl, 7-methyl-2-quinolyl, 2-quinoxalyl, 3-methyl-2-quinoxalyl or 8-quinolyl.

$D^{2A}$ is preferably oxygen or nitrogen, in particular oxygen.

Possible carboorganic substituents $R^{29A}$ and $R^{31A}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups and/or N- or O-containing radicals, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, 2-methoxyphenyl, 2-N,N-dimethylaminophenyl, or arylalkyl which may be substituted by further alkyl groups, e.g. benzyl, o-, m-, p-methylbenzyl, 1- or 2-ethylphenyl where the organic radicals $R^{29A}$ and $R^{31A}$ may also be substituted by halogens such as fluorine, chlorine or bromine. Preference is given to using methyl, phenyl, p-methylphenyl or trifluoromethyl as $R^{29A}$. Particularly useful radicals $R^{31A}$ are $C_1$-$C_{10}$-alkyl such as methyl, ethyl, n-propyl, n-butyl, tert-butyl, n-pentyl, n-hexyl, n-heptyl, n-octyl, phenyl, p-methylphenyl or trifluoromethyl.

In organosilicon substituents $SiR^{30A}_3$ and $SiR^{32A}_3$, the radicals $R^{30A}$ and $R^{32A}$ can be the same radicals described in more detail above for $R^{29A}$, with two radicals $R^{30A}$ or two radicals $R^{32A}$ also being able to be joined to form a 5- or 6-membered ring, e.g. trimethylsilyl, triethylsilyl, butyldimethylsilyl, tributylsilyl, triallylsilyl, triphenylsilyl or dimethylphenylsilyl.

Suitable ligands $X^{2A}$ are, in particular, the halogens fluorine, chlorine, bromine or iodine, in particular chlorine. Alkoxides and sulfonates are also particularly useful ligands $X^{2A}$. The ease and speed with which the group $X^{2A}$ is replaced can be influenced by variation of the radical $R^{29A}$. Thus, a particularly preferred embodiment is a system in which $X^{2A}$ is chlorine, triflate or p-toluenesulfonate.

Suitable ligands $X^{4A}$ are, in particular, the halogens fluorine, chlorine, bromine or iodine, in particular chlorine. Alkoxides and sulfonates are also particularly useful ligands $X^{4A}$. $X^{4A}$ is particularly preferably chlorine, bromine, methoxide, ethoxide, isopropoxide, phenoxide, triflate or p-toluenesulfonate.

$X^{3A}$ is hydrogen or a singly positively charged cation; it is also possible to use doubly charged cations such as magnesium whose second charge is balanced by a further radical $(A$-$D^{2A}R^{27A}_n)$ or by a counterion such as $X^{4A}$. Furthermore, Lewis bases such as diethyl ether or tetrahydrofuran can be coordinated to the cation.

Substituted and unsubstituted cyclopentadiene dystems of the formula (VII) can be prepared, for example, by reacting a substituted or unsubstituted cyclopentadienyl anion with a compound of the formula $SiR^{25A}R^{26A}X^{2A}_2$, for example $(CH_3)_2SiCl_2$. Reactions of this type are described, for example, in EP-659757.

Compounds of the formula $(A^{1A}$-$D^{2A}R^{27A}_n)_p X^{3A}$ are, for example, commercially available, e.g. 2-(methylamino)pyridine, 3-hydroxyisoquinoline, 2-hydroxy-4-methylpyridine, 2-hydroxy-4-methylpyridine, 2-hydroxy-4-methylpyrimidine, 2-hydroxypyridine, 2-hydroxyquinoline or 4-hydroxyquinazoline. The hydrogen atom on $D^{2A}$ can be replaced by $X^{3A}$ (not hydrogen) by deprotonation with a base. As bases, it is possible to use, for example, lithium alkyls, sodium hydride, sodium amides, sodium alkoxides, sodium alkyls, potassium hydride, potassium amides, potassium alkoxides, potassium alkyls, magnesium alkyls, alkylmagnesium halides or mixtures thereof. The molar ratio of base to $(A^{1A}$-$D^{2A}R^{27A}_n)_p X^{3A}$ is usually in the range from 0.4:1 to 100:1, preferably in the range from 0.9:1 to 10:1 and particularly preferably from 0.95:1 to 1.1:1. As solvents in the deprotonation step, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The reactions can be carried out at from $-100$ to $+160°$ C., in particular from $-80$ to $100°$ C. At temperatures above $40°$ C., preference is given to using aromatic or aliphatic solvents which contain no ethers or only small proportions of ethers.

When compounds $(A^{1A}$-$D^{2A}R^{27A}_n)_p H$ are used, a Lewis base, e.g. an amine, can be additionally used if desired. Preference is given to using trialkylamines bearing three $C_1$-$C_{20}$-alkyl radicals. The ratio of Lewis base to $(A^{1A}$-$D^{2A}R^{27A}_n)_p H$ is usually from 0.1:1 to 10:1, preferably from 0.5:1 to 2:1.

As solvents for the reaction of step a), it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The reaction can be carried out at from $-100$ to $+160°$ C., preferably from $-80$ to $100°$ C. and particularly preferably from 0 to $60°$ C. At temperatures above $40°$ C., preference is given to using aromatic or aliphatic solvents which contain no ethers or only small proportions of ethers.

The cyclopentadiene system of the formula (VI) formed in step a) can then be isolated in a subsequent step b), for example by filtering off inorganic by-products and/or distilling off the solvent. Preference is given to a nonaqueous work-up.

The cyclopentadiene system (VI) obtained in this way can then be deprotonated by customary methods, for example by means of potassium hydride or n-butyllithium, and reacted further with the appropriate transition metal compound, e.g. chromium trichloride tris(tetrahydrofuran), to give the corresponding monocyclopentadienyl complex (A). Particularly good yields are obtained when the deprotonation is carried out by means of tert-butyllithium. This has been found to be particularly advantageous when the bridge is substituted by substituents containing more than one carbon atom. Furthermore, the cyclopentadiene system (VI) can also, for example, be reacted directly with chromium amides to give the monocyclopentadienyl complex (A), using a method analogous to that in EP-A-742 046.

This method of preparing the cyclopentadiene systems (VI) is particularly advantageous since it uses simple starter materials and gives good yields.

The monocyclopentadienyl complexes of the present invention can be used either alone or together with further components as catalyst system for olefin polymerization. We have also found catalyst systems for olefin polymerization comprising A) at least one monocyclopentadienyl complex according to the present invention,
B) optionally, an organic or inorganic support,
C) optionally, one or more activating compounds,
D) optionally, one or more catalysts suitable for olefin polymerization and
E) optionally, one or more metal compounds containing a metal of group 1, 2 or 13 of the Periodic Table.

Thus, more than one of the monocyclopentadienyl complexes of the present invention can simultaneously be brought into contact with the olefin or olefins to be polymerized. This has the advantage that a wide range of polymers can be produced in this way. For example, bimodal products can be prepared in this way.

For the monocyclopentadienyl complexes of the present invention to be able to be used in polymerization processes in the gas phase or in suspension, it is often advantageous to use them in the form of a solid, i.e. for them to be applied to a solid support B). Furthermore, the supported monocyclopentadienyl complexes have a high productivity. The monocyclopentadienyl complexes of the present invention can therefore also, if desired, be immobilized on an organic or inorganic support B) and used in supported form in the polymerization. This enables, for example, deposits in the reactor to be avoided and the polymer morphology to be controlled. As support materials, preference is given to using silica gel, magnesium chloride, aluminum oxide, mesoporous materials, aluminosilicates, hydrotalcites and organic polymers such as polyethylene, polypropylene, polystyrene, polytetrafluoroethylene or polar functionalized polymers, e.g. copolymers of ethene and acrylic esters, acrolein or vinyl acetate.

Particular preference is given to a catalyst system comprising a monocyclopentadienyl complex according to the present invention and at least one activating compound C) and also a support component B).

To obtain such a supported catalyst system, the unsupported catalyst system can be reacted with a support component B). The order in which the support component B), the monocyclopentadienyl complex A) of the present invention and the activating compound C) are combined is in principle immaterial. The monocyclopentadienyl complex A) of the present invention and the activating compound C) can be fixed to the support independently of one another or simultaneously. After the individual process steps, the solid can be washed with suitable inert solvents such as aliphatic or aromatic hydrocarbons.

In a preferred method of preparing the supported catalyst system, at least one of the monocyclopentadienyl complexes of the present invention is brought into contact with at least one activating compound C) in a suitable solvent, preferably giving a soluble reaction product, an adduct or a mixture. The preparation obtained in this way is then mixed with the dehydrated or passivated support material, the solvent is removed and the resulting supported monocyclopentadienyl complex catalyst system is dried to ensure that all or most of the solvent has been removed from the pores of the support material. The supported catalyst is obtained as a free-flowing powder. Examples of the industrial implementation of the above process are described in WO 96/00243, WO 98/40419 or WO 00/05277. A further preferred embodiment comprises firstly applying the activating compound C) to the support component B) and subsequently bringing this supported compound into contact with the monocyclopentadienyl complex A) of the present invention.

As support component B), preference is given to using finely divided supports which can be any organic or inorganic solids. In particular, the support component B) can be a porous support such as talc, a sheet silicate such as montmorillonite or mica, an inorganic oxide or a finely divided polymer powder (e.g. a polyolefin or a polymer having polar functional groups).

The support materials used preferably have a specific surface area in the range from 10 to 1 000 m$^2$/g, a pore volume in the range from 0.1 to 5 ml/g and a mean particle size of from 1 to 500 µm. Preference is given to supports having a specific surface area in the range from 50 to 700 m$^2$/g, a pore volume in the range from 0.4 to 3.5 ml/g and a mean particle size in the range from 5 to 350 µm. Particular preference is given to supports having a specific surface area in the range from 200 to 550 m$^2$/g, a pore volume in the range from 0.5 to 3.0 ml/g and a mean particle size of from 10 to 150 µm.

The inorganic support can be subjected to a thermal treatment, e.g. to remove adsorbed water. Such a drying treatment is generally carried out at from 80 to 300° C., preferably from 100 to 200° C. Drying at from 100 to 200° C. is preferably carried out under reduced pressure and/or under a blanket of inert gas (e.g. nitrogen), or the inorganic support can be calcined at from 200 to 1000° C. to produce the desired structure of the solid and/or set the desired OH concentration on the surface. The support can also be treated chemically using customary desiccants such as metal alkyls, preferably aluminum alkyls, chlorosilanes or SiCl$_4$, or else methylaluminoxane. Appropriate treatment methods are described, for example, in WO 00/31090.

The inorganic support material can also be chemically modified. For example, the treatment of silica gel with NH$_4$SiF$_6$ or other fluorinating agents leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by appropriate purification and drying operations before use. It is also possible to use functionalized polymer supports, e.g. ones based on polystyrene, polyethylene or polypropylene, via whose functional groups, for example ammonium or hydroxy groups, at least one of the catalyst components can be fixed.

Inorganic oxides suitable as support component B) may be found among the oxides of elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium or titanium and also corresponding oxide mixtures. Other inorganic oxides which can be used alone or in combination with the abovementioned preferred oxidic supports are, for example, MgO, CaO, AlPO$_4$, ZrO$_2$, TiO$_2$, B$_2$O$_3$ or mixtures thereof.

As solid support materials B) for catalysts for olefin polymerization, preference is given to using silica gels since particles whose size and structure make them suitable as supports for olefin polymerization can produced from this material. Spray-dried silica gels comprising spherical agglomerates of smaller granular particles, i.e. primary particles, have been found to be particularly useful. The silica gels can be dried and/or calcined before use.

Further preferred supports B) are hydrotalcites and calcined hydrotalcites. In mineralogy, hydrotalcite is a natural mineral having the ideal formula

whose structure is derived from that of brucite Mg(OH)$_2$. Brucite crystallizes in a sheet structure with the metal ions in octahedral holes between two layers of close-packed hydroxyl ions, with only every second layer of the octahedral holes being occupied. In hydrotalcite, some magnesium ions are replaced by aluminum ions, as a result of which the packet of layers gains a positive charge. This is compensated by the anions which are located together with water of crystallization in the layers in between.

Such sheet structures are found not only in magnesium-aluminum hydroxides, but also generally in mixed metal hydroxides of the formula

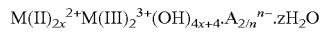

which have a sheet structure and in which M(II) is a divalent metal such as Mg, Zn, Cu, Ni, Co, Mn, Ca and/or Fe and M(III) is a trivalent metal such as Al, Fe, Co, Mn, La, Ce and/or Cr, x is from 0.5 to 10 in steps of 0.5, A is an interstitial anion and n is the charge on the interstitial anion which can be from 1 to 8, usually from 1 to 4, and z is an integer from 1 to 6, in particular from 2 to 4. Possible interstitial anions are organic anions such as alkoxide anions, alkyl ether sulfates, aryl ether sulfates or glycol ether sulfates, inorganic anions such as, in particular, carbonate, hydrogencarbonate, nitrate, chloride, sulfate or B(OH)$_4^-$ or polyoxo metal anions such as $Mo_7O_{24}^{6-}$ or $V_{10}O_{28}^{6-}$. However, a mixture of a plurality of such anions can also be present.

Accordingly, all such mixed metal hydroxides having a sheet structure should be regarded as hydrotalcites for the purposes of the present invention.

Calcined hydrotalcites can be prepared from hydrotalcites by calcination, i.e. heating, by means of which the desired hydroxyl group content can be set. In addition, the crystal structure also changes. The preparation of the calcined hydrotalcites used according to the present invention is usually carried out at temperatures above 180° C. Preference is given to calcination for from 3 to 24 hours at from 250° C. to 1000° C., in particular from 400° C. to 700° C. It is possible for air or inert gas to be passed over the solid during calcination or for a vacuum to be applied.

On heating, the natural or synthetic hydrotalcites firstly give off water, i.e. drying occurs. On further heating, the actual calcination, the metal hydroxides are converted into the metal oxides by elimination of hydroxyl groups and interstitial anions; OH groups or interstitial anions such as carbonate can also still be present in the calcined hydrotalcites. A measure of this is the loss on ignition. This is the weight loss experienced by a sample which is heated in two steps firstly for 30 minutes at 200° C. in a drying oven and then for 1 hour at 950° C. in a muffle furnace.

The calcined hydrotalcites used as component B) are thus mixed oxides of the divalent and trivalent metals M(II) and M(III), with the molar ratio of M(II) to M(III) generally being in the range from 0.5 to 10, preferably from 0.75 to 8 and in particular from 1 to 4. Furthermore, normal amounts of impurities, for example Si, Fe, Na, Ca or Ti and also chlorides and sulfates, can also be present.

Preferred calcined hydrotalcites B) are mixed oxides in which M(II) is magnesium and M(III) is aluminum. Such aluminum-magnesium mixed oxides are obtainable from Condea Chemie GmbH (now Sasol Chemie), Hamburg, under the trade name Puralox Mg.

Preference is also given to calcined hydrotalcites in which the structural transformation is complete or virtually complete. Calcination, i.e. transformation of the structure, can be confirmed, for example, by means of X-ray diffraction patterns.

The hydrotalcites, calcined hydrotalcites or silica gels employed are generally used as finely divided powders having a mean particle diameter $d_{50}$ of from 5 to 200 μm, preferably from 10 to 150 μm, particularly preferably from 15 to 100 μm and in particular from 20 to 70 μm, and usually have pore volumes of from 0.1 to 10 cm³/g, preferably from 0.2 to 5 cm³/g, and specific surface areas of from 30 to 1 000 m²/g, preferably from 50 to 800 m²/g and in particular from 100 to 600 m²/g. The monocyclopentadienyl complexes of the present invention are preferably applied in such an amount that the concentration of transition metal complex in the finished catalyst system is from 5 to 200 μmol, preferably from 20 to 100 μmol and particularly preferably from 25 to 70 μmol per g of support B).

Some of the monocyclopentadienyl complexes of the present invention have little polymerization activity on their own and are then brought into contact with an activator, viz. the component C), in order to be able to display good polymerization activity. For this reason, the catalyst system optionally further comprises, as component C), one or more activating compounds, preferably at least one cation-forming compound C).

Suitable compounds C) which are able to react with the monocyclopentadienyl complex A) to convert it into a catalytically active, or more active, compound are, for example, compounds such as an aluminoxane, a strong uncharged Lewis acid, an ionic compound having a Lewis-acid cation or an ionic compound containing a Brönsted acid as cation.

As aluminoxanes, it is possible to use, for example, the compounds described in WO 00/31090. Particularly useful aluminoxanes are open-chain or cyclic aluminoxane compounds of the formula (X) or (XI)

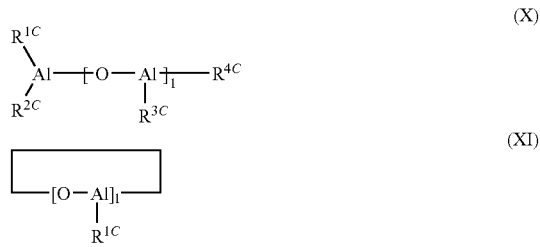

where $R^{1C}$-$R^{4C}$ are each, independently of one another, a $C_1$-$C_6$-alkyl group, preferably a methyl, ethyl, butyl or isobutyl group and I is an integer from 1 to 30, preferably from 5 to 25.

A particularly useful aluminoxane compound is methylaluminoxane.

These oligomeric aluminoxane compounds are usually prepared by controlled reaction of a solution of trialkylaluminum with water. In general, the oligomeric aluminoxane compounds obtained in this way are in the form of mixtures of both linear and cyclic chain molecules of various lengths, so that I is to be regarded as a mean. The aluminoxane compounds can also be present in admixture with other metal alkyls, usually aluminum alkyls. Aluminoxane preparations suitable as component C) are commercially available.

Furthermore, modified aluminoxanes in which some of the hydrocarbon radicals have been replaced by hydrogen atoms or alkoxy, aryloxy, siloxy or amide radicals can also be used as component C) in place of the aluminoxane compounds of the formula (X) or (XI).

It has been found to be advantageous to use the monocyclopentadienyl complexes A) and the aluminoxane compounds in such amounts that the atomic ratio of aluminum from the aluminoxane compounds including any aluminum alkyl still present to the transition metal from the monocyclopentadienyl complex A) is in the range from 1:1 to 1 000:1, preferably from 10:1 to 500:1 and in particular in the range from 20:1 to 400:1.

A further class of suitable activating components C) are hydroxyaluminoxanes. These can be prepared, for example, by addition of from 0.5 to 1.2 equivalents of water, preferably from 0.8 to 1.2 equivalents of water, per equivalent of aluminum to an alkylaluminum compound, in particular triisobutylaluminum, at low temperatures, usually below 0° C. Such compounds and their use in olefin polymerization are described, for example, in WO 00/24787. The atomic ratio of aluminum from the hydroxyaluminoxane compound to the transition metal from the monocyclopentadienyl complex A) is usually in the range from 1:1 to 100:1, preferably from 10:1 to 50:1 and in particular in the range from 20:1 to 40:1. Preference in this case is given to using a monocyclopentadienyl metal dialkyl compound A).

As strong, uncharged Lewis acids, preference is given to compounds of the formula (XII)

where $M^{1C}$ is an element of group 13 of the Periodic Table of the Elements, in particular B, Al or Ga, preferably B, $X^{1C}$, $X^{2C}$ and $X^{3C}$ are each hydrogen, $C_1$-$C_{10}$alkyl, $C_6$-$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryls, preferably pentafluorophenyl.

Further examples of strong, uncharged Lewis acids are given in WO 00/31090.

Compounds of this type which are particularly useful as component C) are boranes and boroxins such as trialkylborane, triarylborane or trimethylboroxin. Particular preference is given to using boranes which bear at least two perfluorinated aryl radicals. Particular preference is given to compounds of the formula (XII) in which $X^{1C}$, $X^{2C}$ and $X^{3C}$ are identical, preferably tris(pentafluorophenyl)borane.

Suitable compounds C) are preferably prepared by reaction of aluminum or boron compounds of the formula (XII) with water, alcohols, phenol derivatives, thiophenol derivatives or aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4,4',5,5',6,6'-nonafluorobiphenyl. Examples of combinations of compounds of the formula (XII) with Brönsted acids are, in particular, trimethylaluminum/pentafluorophenol, trimethylaluminum/1-bis(pentafluorophenyl)methanol, trimethylaluminum/4-hydroxy-2,2',3,3',4,4',5,5',6,6'-nonafluorobiphenyl, triethylaluminum/pentafluorophenol and triisobutylaluminum/pentafluorophenol and triethylaluminum/4,4'-dihydroxy-2,2',3,3',5,5',6,6'-octafluorobiphenyl hydrate.

In further suitable aluminum and boron compounds of the formula (XII), $X^{1C}$ is an OH group. Examples of compounds of this type are boronic acids and borinic acids, in particular borinic acids having perfluorinated aryl radicals, for example $(C_6F_5)_2BOH$.

Strong uncharged Lewis acids suitable as activating compounds C) also include the reaction products of a boronic acid with two equivalents of an aluminum trialkyl or the reaction products of an aluminum trialkyl with two equivalents of an acidic fluorinated, in particular perfluorinated, hydrocarbon compound such as pentafluorophenol or bis(pentafluorophenyl)borinic acid.

Suitable ionic compounds having Lewis-acid cations include salt-like compounds of the cation of the formula (XIII)

where $M^{2C}$ is an element of groups 1 to 16 of the Periodic Table of the Elements, $Q_1$ to $Q_z$ are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups, a is an integer from 1 to 6 and z is an integer from 0 to 5, d corresponds to the difference a–z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by combining a boron or aluminum compound, e.g. an aluminum alkyl, with a second compound which can react to link two or more boron or aluminum atoms, e.g. water, and a third compound which forms an ionizing ionic compound with the boron or aluminum compound, e.g. triphenylchloromethane, or optionally a base, preferably an organic nitrogen-containing base, for example an amine, an aniline derivative or a nitrogen heterocycle. In addition, a fourth compound which likewise reacts with the boron or aluminum compound, e.g. pentafluorophenol, can be added.

Ionic compounds containing Brönsted acids as cations preferably likewise have noncoordinating counterions. As Brönsted acid, particular preference is given to protonated amine or aniline derivatives. Preferred cations are N,N-dimethylanilinium, N,N-dimethylcyclohexylammonium and N,N-dimethylbenzylammonium and also derivatives of the latter two.

Compounds containing anionic boron heterocycles as are described in WO 97/36937 are also suitable as component C), in particular dimethylanilinium boratabenzene or trityl boratabenzene.

Preferred ionic compounds C) contain borates which bear at least two perfluorinated aryl radicals. Particular preference is given to N,N-dimethylanilinium tetrakis(pentafluorophenyl)borate and in particular N,N-dimethylcyclohexylammonium tetrakis(pentafluorophenyl)borate, N,N-dimethylbenzylammonium tetrakis(pentafluorophenyl)borate or trityl tetrakispentafluorophenylborate.

It is also possible for two or more borate anions and/or boranes to be joined to one another or a borate anion to be joined to a borane, as in the dianion $[(C_6F_5)_3B—C_6F_4—B(C_6F_5)_3]^{2-}$ or the anion $(C_6F_5)_3B—CN—B(C_6F_5)_3]^-$, or the borate anion can be bound via a bridge having a suitable functional group to the support surface.

Further suitable activating compounds C) are listed in WO 00/31090.

The amount of strong, uncharged Lewis acids, ionic compounds having Lewis-acid cations or ionic compounds containing Brönsted acids as cations is preferably from 0.1 to 20 equivalents, more preferably from 1 to 10 equivalents, based on the monocyclopentadienyl complex A).

Suitable activating compounds C) also include boron-aluminum compounds such as di[bis(pentafluorophenyl)boroxy]methylalane. Examples of such boron-aluminum compounds are those disclosed in WO 99/06414.

It is also possible to use mixtures of all the abovementioned activating compounds C). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Both the monocyclopentadienyl complexes A) and the activating compounds C) are preferably used in a solvent, preferably an aromatic hydrocarbon having from 6 to 20 carbon atoms, in particular xylenes, toluene, pentane, hexane, heptane or a mixture thereof.

A further possibility is to use an activating compound C) which can simultaneously be employed as support B). Such systems are obtained, for example, from an inorganic oxide by treatment with zirconium alkoxide and subsequent chlorination, for example by means of carbon tetrachloride. The preparation of such systems is described, for example, in WO 01/41920.

A likewise broad product spectrum can be achieved by use of the monocyclopentadienyl complexes A) of the present invention in combination with at least one further catalyst D) which is suitable for the polymerization of olefins. It is therefore possible to use one or more catalysts suitable for olefin polymerization as optional component D) in the catalyst system. Possible catalysts D) are, in particular, classical Ziegler-Natta catalysts based on titanium and classical Phillips catalysts based on chromium oxides.

Possible components D) are in principle all compounds of transition metals of groups 3 to 12 of the Periodic Table or the lanthanides which contain organic groups and preferably form active catalysts for olefin polymerization after reaction with the components C) in the presence of A) and optionally B) and/or E). These are usually compounds in which at least one monodentate or polydentate ligand is bound to the central atom via a sigma or pi bond. Possible ligands include both ligands containing cyclopentadienyl groups and ligands which are free of cyclopentadienyl groups. A large number of such compounds D) suitable for olefin polymerization are described in Chem. Rev. 2000, vol. 100, No. 4. Furthermore, multinuclear cyclopentadienyl complexes are also suitable for olefin polymerization.

Particularly well-suited components D) include compounds having at least one cyclopentadienyl ligand, which are generally referred to as metallocene complexes. Particularly useful metallocene complexes are those of the formula (XIV)

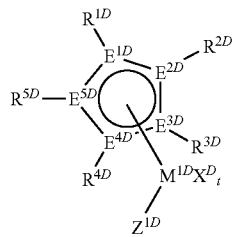

(XIV)

where the substituents and indices have the following meanings:

$M^{1D}$ is titanium, zirconium, hafnium, vanadium, niobium, tantalum, chromium, molybdenum or tungsten, or an element of group 3 of the Periodic Table and the lanthanides, $X^D$ is fluorine, chlorine, bromine, iodine, hydrogen, $C_1$-$C_{10}$-alkyl, $C_2$-$C_{10}$-alkenyl, $C_6$-$C_{15}$-aryl, arylalkyl having from 1 to 10 carbon atoms in the alkyl part and from 6 to 20 carbon atoms in the aryl part, —$OR^{6D}$ or —$NR^{6D}R^{7D}$, or two radicals $X^D$ form a substituted or unsubstituted diene ligand, in particular a 1,3-diene ligand, and the radicals $X^D$ are identical or different and may be joined to one another, $E^{1D}$-$E^{5D}$ are each carbon or not more than one $E^{1D}$ to $E^{5D}$ is phosphorus or nitrogen, preferably carbon, t is 1, 2 or 3 and is such that, depending on the valence of $M^{1D}$, the metallocene complex of the formula (XIV) is uncharged, where $R^{6D}$ and $R^{7D}$ are each $C_1$-$C_{10}$-alkyl, $C_6$-$C_{15}$-aryl, alkylaryl, arylalkyl, fluoroalkyl or fluoroaryl, each having from 1 to 10 carbon atoms in the alkyl radical and from 6 to 20 carbon atoms in the aryl radical, and $R^{1D}$ to $R^{5D}$ are each, independently of one another, hydrogen, $C_1$-$C_{22}$-alkyl, 5- to 7-membered cycloalkyl or cycloalkenyl which may in turn bear $C_1$-$C_{10}$-alkyl groups as substituents, $C_2$-$C_{22}$-alkenyl, $C_6$-$C_{22}$-aryl, arylalkyl having from 1 to 16 carbon atoms in the alkyl part and 6-21 carbon atoms in the aryl part, $NR^{8D}_2$, $N(SiR^{8D}_3)_2$, $OR^{8D}$, $OSiR^{8D}_3$, $SiR^{8D}_3$, where the organic radicals $R^{1D}$-$R^{5D}$ may also be substituted by halogens and/or two radicals $R^{1D}$-$R^{5D}$, in particular vicinal radicals, may also be joined to form a five-, six- or seven-membered ring, and/or two vicinal radicals $R^{1D}$-$R^{5D}$ may be joined to form a five-, six- or seven-membered heterocycle which contains at least one atom from the group consisting of N, P, O and S, where the radicals $R^{8D}$ can be identical or different and are each $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy and $Z^{1D}$ is as defined for $X^D$ or is

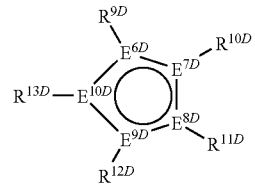

where the radicals $R^{9D}$ to $R^{13D}$ are each, independently of one another, hydrogen, $C_1$-$C_{22}$-alkyl, 5- to 7-membered cycloalkyl or cycloalkenyl which may in turn bear $C_1$-$C_{10}$-alkyl groups as substituents, $C_2$-$C_{22}$alkenyl, $C_6$-$C_{22}$-aryl, arylalkyl having from 1 to 16 carbon atoms in the alkyl part and 6-21 carbon atoms in the aryl part, $NR^{14D}_2$, $N(SiR^{14D}_3)_2$, $OR^{14D}$, $OSiR^{14D}_3$, $SiR^{14D}_3$, where the organic radicals $R^{9D}$-$R^{13D}$ may also be substituted by halogens and/or two radicals $R^{9D}$-$R^{13D}$, in particular vicinal radicals, may also be joined to form a five-, six- or seven-membered ring, and/or two vicinal radicals $R^{9D}$-$R^{13D}$ may be joined to form a five-, six- or seven-membered heterocycle containing at least one atom from the group consisting of N, P, O and S, where the radicals $R^{14D}$ are identical or different and are each $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy, $E^{6D}$-$E^{10D}$ are each carbon or not more than one $E^{6D}$ to $E^{10D}$ is phosphorus or nitrogen, preferably carbon or the radicals $R^{4D}$ and $Z^{1D}$ together form an —$R^{15D}_v$-$A^{1D}$- group in which $R^{15D}$ is

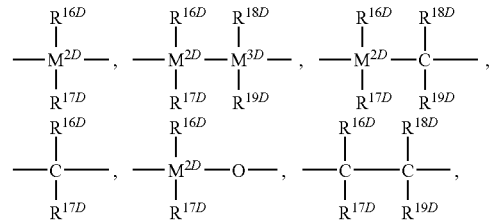

-continued

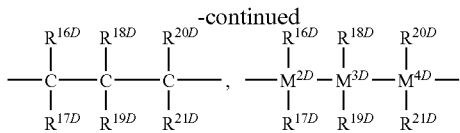

$=BR^{16D}$, $=BNR^{16D}R^{17D}$, $=AlR^{16D}$, —Ge—, —Sn—, —O—, $=SO$, $=SO_2$, $=NR^{16D}$, $=CO$, $=PR^{16D}$ or $=P(O)R^{16D}$ where $R^{16D}$-$R^{21D}$ are identical or different and are each a hydrogen atom, a halogen atom, a trimethylsilyl group, a $C_1$-$C_{10}$alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-alkoxy group, a $C_7$-$C_{15}$-alkylaryloxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them form a saturated or unsaturated ring having from 4 to 15 carbon atoms, and $M^{2D}$-$M^{4D}$ is silicon, germanium or tin, preferably silicon $A^{1D}$ is

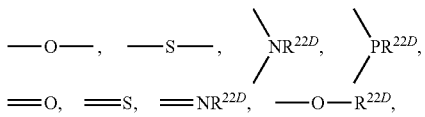

—$NR^{22D}_2$, —$PR^{22D}_2$ or an unsubstituted, substituted or fused, heterocyclic ring system, where the radicals $R^{22D}$ are each, independently of one another, $C_1$-$C_{10}$alkyl, $C_6$-$C_{15}$-aryl, $C_3$-$C_{10}$-cycloalkyl, $C_7$-$C_{18}$-arylalkyl or $Si(R^{23D})_3$, $R^{23D}$ is hydrogen, $C_1$-$C_{10}$-alkyl, $C_6$-$C_{15}$-aryl which may in turn bear $C_1$-$C_4$-alkyl groups as substituents or $C_3$-$C_{10}$-cycloalkyl, is 1 or when $A^{1D}$ is an unsubstituted, substituted or fused, heterocyclic ring system may also be 0, or the radicals $R^{4D}$ and $R^{12D}$ together form an —$R^{15D}$— group.

$A^{1D}$ together with the bridge $R^{15D}$ can, for example, form an amine, ether, thioether or phosphine. However, $A^{1D}$ may also be an unsubstituted, substituted or fused, heterocyclic aromatic ring system which can contain heteroatoms from the group consisting of oxygen, sulfur, nitrogen and phosphorus in addition to carbon atoms in the ring. Examples of 5-membered heteroaryl groups which can contain from one to four nitrogen atoms and/or a sulfur or oxygen atom as ring atoms in addition to carbon atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups, which can contain from one to four nitrogen atoms and/or a phosphorus atom, are 2-pyridinyl, 2-phosphabenzolyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 5-membered and 6-membered heteroaryl groups can also be substituted by $C_1$-$C_{10}$-alkyl, $C_6$-$C_{10}$-aryl, arylalkyl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Naming and numbering of the heterocycles has been taken from L. Fieser and M. Fieser, Lehrbuch der organischen Chemie, 3rd revised edition, Verlag Chemie, Weinheim 1957.

It is preferred that the radicals $X^D$ in the formula (XIV) are identical, preferably fluorine, chorine, bromine, $C_1$-$C_7$-alkyl or aralkyl, in particular chlorine, methyl or benzyl.

The synthesis of such complexes can be carried out by methods known per se, preferably by reacting the appropriately substituted, cyclic hydrocarbon anions with halides of titanium, zirconium, hafnium or chromium.

Among the metallocene complexes of the formula (XIV), preference is given to

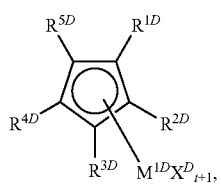
(XIVa)

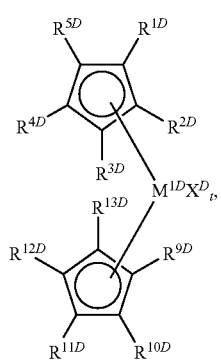
(XIVb)

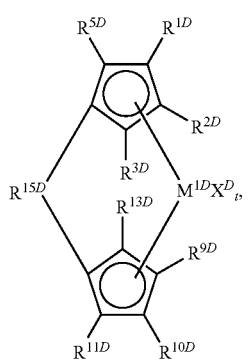
(XIVc)

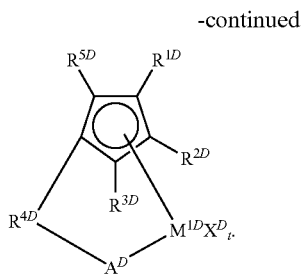

Among the compounds of the formula (XIVa), particular preference is given to those in which
$M^{1D}$ is titanium, vanadium or chromium,
$X^D$ is chlorine, $C_1$-$C_4$-alkyl, phenyl, alkoxy or aryloxy,
t is 1 or 2 and
$R^{1D}$ to $R^{5D}$ are each hydrogen, $C_1$-$C_6$-alkyl or two adjacent radicals $R^{1D}$ to $R^{5D}$ form a substituted or unsubstituted benzo group.

Among the compounds of the formula (XIVb), preference is given to those in which
$M^{1D}$ is titanium, zirconium, vanadium, hafnium or chromium,
$X^D$ is fluorine, chlorine, $C_1$-$C_4$-alkyl or benzyl, or two radicals $X^D$ form a substituted or unsubstituted butadiene ligand,
t is 0 in the case of chromium, otherwise 1 or 2, preferably 2,
$R^{1D}$ to $R^{5D}$ are each hydrogen, $C_1$-$C_8$-alkyl, $C_6$-$C_8$-aryl, $NR^{8D}_2$, $OSiR^{8D}_3$ or $Si(R^{8D})_3$ and
$R^{9D}$ to $R^{13D}$ are each hydrogen, $C_1$-$C_8$-alkyl or $C_6$-$C_8$-aryl, $NR^{14D}_2$, $OSiR^{14D}_3$ or $Si(R^{14D})_3$ or two radicals $R^{1D}$ to $R^{5D}$ and/or $R^{9D}$ to $R^{13D}$ together with the $C_5$ ring form an indenyl, fluorenyl or substituted indenyl or fluorenyl system.

The compounds of the formula (XIVb) in which the cyclopentadienyl radicals are identical are particularly useful.

Examples of particularly useful compounds D) of the formula (XIVb) include: bis(cyclopentadienyl)chromium, bis(indenyl)titanium dichloride, bis(fluorenyl)titanium dichloride, bis(tetrahydroindenyl)titanium dichloride, bis(pentamethylcyclopentadienyl)titanium dichloride, bis(trimethylsilylcyclopentadienyl)titanium dichloride, bis(trimethoxysilylcyclopentadienyl)titanium dichloride, bis(isobutylcyclopentadienyl)titanium dichloride, bis(3-butenylcyclopentadienyl)titanium dichloride, bis(methylcyclopentadienyl)titanium dichloride, bis(1,3-di-tert-butylcyclopentadienyl)titanium dichloride, bis(trifluoromethylcyclopentadienyl)titanium dichloride, bis(tert-butylcyclopentadienyl)titanium dichloride, bis(n-butylcyclopentadienyl)titanium dichloride, bis(phenylcyclopentadienyl)titanium dichloride, bis(N,N-dimethylaminomethylcyclopentadienyl)titanium dichloride, bis(1,3-dimethylcyclopentadienyl)titanium dichloride, bis(1-methyl-3-n-butylcyclopentadienyl)titanium dichloride, (cyclopentadienyl)(methylcyclopentadienyl)titanium dichloride, (cyclopentadienyl)(n-butylcyclopentadienyl)titanium dichloride, (methylcyclopentadienyl)(n-butylcyclopentadienyl)titanium dichloride, (cyclopentadienyl)(1-methyl-3-n-butylcyclopentadienyl)titanium dichloride, bis(cyclopentadienyl)zirconium dichloride, bis(pentamethylcyclopentadienyl)zirconium dichloride, bis(methylcyclopentadienyl)zirconium dichloride, bis(ethylcyclopentadienyl)zirconium dichloride, bis(n-butylcyclopentadienyl)zirconium dichloride, bis(tert-butylcyclopentadienyl)zirconium dichloride, bis(isobutylcyclopentadienyl)zirconium dichloride, bis(3-butenylcyclopentadienyl)zirconium dichloride, bis(trifluoromethylcyclopentadienyl)zirconium dichloride, bis(phenylcyclopentadienyl)zirconium dichloride, bis(1,3-dimethylcyclopentadienyl)zirconium dichloride, bis(1-n-butyl-3-methylcyclopentadienyl)zirconium dichloride, bis(1,3-di-tert-butylcyclopentadienyl)zirconium dichloride, bis(tetramethylcyclopentadienyl)zirconium dichloride, bis(indenyl)zirconium dichloride, bis(tetrahydroindenyl)zirconium dichloride, bis(fluorenyl)zirconium dichloride, (cyclopentadienyl)(methylcyclopentadienyl)zirconium dichloride, (cyclopentadienyl)(n-butylcyclopentadienyl)zirconium dichloride, (methylcyclopentadienyl)(n-butylcyclopentadienyl)zirconium dichloride, (cyclopentadienyl)(1-methyl-3-n-butylcyclopentadienyl)zirconium dichloride, bis(trimethoxysilylcyclopentadienyl)zirconium dichloride and bis(trimethylsilylcyclopentadienyl)zirconium dichloride, and also the corresponding dimethylzirconium compounds.

Particularly useful compounds of the formula (XIVc) are those in which
$R^{15D}$ is

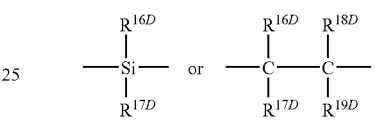

or $=BR^{16D}$ or $=BNR^{16D}R^{17D}$,
$M^{1D}$ is titanium, zirconium or hafnium, in particular zirconium, and
the radicals $X^D$ are identical or different and are each chlorine, $C_1$-$C_4$-alkyl, benzyl, phenyl or $C_7$-$C_{15}$-alkylaryloxy.

Particularly useful compounds of the formula (XIVc) are those of the formula (XIVc')

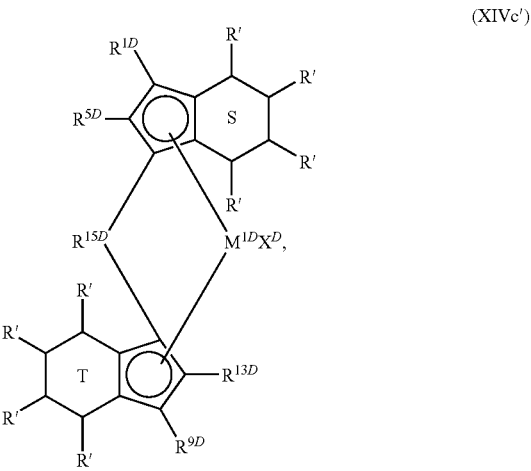

where
the radicals R' are identical or different and are each hydrogen, $C_1$-$C_{10}$-alkyl or $C_3$-$C_{10}$-cycloalkyl, preferably methyl, ethyl, isopropyl or cyclohexyl, $C_6$-$C_{20}$-aryl, preferably phenyl, naphthyl or mesityl, $C_7$-$C_{40}$-arylalkyl, $C_7$-$C_{40}$-alkylaryl, preferably 4-tert-butylphenyl or 3,5-di-tert-butylphenyl, or $C_8$-$C_{40}$-arylalkenyl,
$R^{5D}$ and $R^{13D}$ are identical or different and are each hydrogen, $C_1$-$C_6$-alkyl, preferably methyl, ethyl, isopropyl, n-propyl, n-butyl, n-hexyl or tert-butyl, and the rings S and T may be identical or different and saturated, unsaturated or partially saturated.

The indenyl or tetrahydroindenyl ligands of the metallocenes of the formula (XIVc') are preferably substituted in the 2 position, the 2,4 positions, the 4,7 positions, the 2,4,7 positions, the 2,6 positions, the 2,4,6 positions, the 2,5,6 positions, the 2,4,5,6 positions or the 2,4,5,6,7 positions, in particular in the 2,4 positions, with the following numbering applying to the site of substitution:

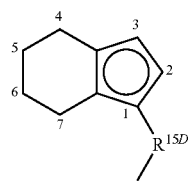

Furthermore, preference is given to using bridged bis-indenyl complexes in the rac or pseudo-rac form as component D). The term "pseudo-rac form" refers to complexes in which the two indenyl ligands are in the rac arrangement relative to one another when all other substituents of the complex are disregarded.

Further examples of particularly useful catalysts D) (XIVc) and (XIVc') include: methylenebis(cyclopentadienyl)zirconium dichloride, methylenebis(3-methylcyclopentadienyl)zirconium dichloride, methylenebis(3-n-butylcyclopentadienyl)zirconium dichloride, methylenebis(indenyl) zirconium dichloride, methylenebis(tetrahydroindenyl) zirconium dichloride, isopropylidenebis(cyclopentadienyl) zirconium dichloride, isopropylidenebis(3-trimethylsilylcyclopentadienyl)zirconium dichloride, isopropylidenebis(3-methylcyclopentadienyl)zirconium dichloride, isopropylidenebis(3-n-butylcyclopentadienyl) zirconium dichloride, isopropylidenebis(3-phenylcyclopentadienyl)zirconium dichloride, isopropylidenebis(indenyl) zirconium dichloride, isopropylidenebis(tetrahydroindenyl) zirconium dichloride, dimethylsilanediylbis (cyclopentadienyl)zirconium dichloride, dimethylsilanediylbis(indenyl)zirconium dichloride, dimethylsilanediylbis(tetrahydroindenyl)zirconium dichloride, ethylenebis(cyclopentadienyl)zirconium dichloride, ethylenebis(indenyl)zirconium dichloride, ethylenebis(tetrahydroindenyl)zirconium dichloride, tetramethylethylene-9-fluorenylcyclopentadienylzirconium dichloride, dimethylsilanediylbis(tetramethylcyclopentadienyl)zirconium dichloride, dimethylsilanediylbis(3-trimethylsilylcyclopentadienyl)zirconium dichloride, dimethylsilanediylbis (3-methylcyclopentadienyl)zirconium dichloride, dimethylsilanediylbis(3-n-butylcyclopentadienyl)zirconium dichloride, dimethylsilanediylbis(3-tert-butyl-5-methylcyclopentadienyl)zirconium dichloride, dimethylsilanediylbis (3-tert-butyl-5-ethylcyclopentadienyl)zirconium dichloride, dimethylsilanediylbis(2-methylindenyl)zirconium dichloride, dimethylsilanediylbis(2-isopropylindenyl)zirconium dichloride, dimethylsilanediylbis(2-tert-butylindenyl)zirconium dichloride, diethylsilanediylbis(2-methylindenyl)zirconium dibromide, dimethylsilanediylbis(3-methyl-5-methylcyclopentadienyl)zirconium dichloride, dimethylsilanediylbis(3-ethyl-5-isopropylcyclopentadienyl) zirconium dichloride, dimethylsilanediylbis(2-ethylindenyl) zirconium dichloride, dimethylsilanediylbis(2-methyl-4,5-benzindenyl)zirconium dichloride, dimethylsilanediylbis(2-ethyl-4,5-benzindenyl)zirconium dichloride, methylphenylsilanediylbis(2-methyl-4,5-benzindenyl)zirconium dichloride, methylphenylsilanediylbis(2-ethyl-4,5-benzindenyl)zirconium dichloride, diphenylsilanediylbis(2-methyl-4,5-benzindenyl)zirconium dichloride, diphenylsilanediylbis(2-ethyl-4,5-benzindenyl)zirconium dichloride, diphenylsilanediylbis(2-methylindenyl)hafnium dichloride, dimethylsilanediylbis(2-methyl-4-phenyl-indenyl)zirconium dichloride, dimethylsilanediylbis(2-ethylphenylindenyl)zirconium dichloride, dimethylsilanediylbis(2-methyl-4-(1-naphthyl)indenyl)zirconium dichloride, dimethylsilanediylbis(2-ethyl-4-(1-naphthyl)indenyl)zirconium dichloride, dimethylsilanediylbis(2-propyl-4-(1-naphthyl)indenyl)zirconium dichloride, dimethylsilanediylbis-(2-i-butyl-4-(1-naphthyl)indenyl)zirconium dichloride, dimethylsilanediylbis(2-propyl-4-(9-phenanthryl)indenyl) zirconium dichloride, dimethylsilanediylbis(2-methyl-4-isopropylindenyl)zirconium dichloride, dimethylsilanediylbis (2,7-dimethyl-4 isopropylindenyl)zirconium dichloride, dimethylsilanediylbis(2-methyl-4,6-diisopropylindenyl)zirconium dichloride, dimethylsilanediylbis(2-methyl-4[p-trifluoromethylphenyl]indenyl)zirconium dichloride, dimethylsilanediylbis(2-methyl-4-[3',5'-dimethylphenyl]indenyl) zirconium dichloride, dimethylsilanediylbis(2-methyl-4-[4'-tert.butylphenyl]indenyl)zirconium dichloride, diethylsilanediylbis(2-methyl-4-[4'-tert-butylphenyl]-indenyl)zirconium dichloride, dimethylsilanediylbis(2-ethyl-4-[4'-tert-butylphenyl]indenyl)zirconium dichloride, dimethylsilanediylbis(2-propyl-4-[4'-tert-butylphenyl]indenyl) zirconium dichloride, dimethylsilanediylbis(2-isopropyl-4-[4'-tert-butylphenyl]indenyl)zirconium dichloride, dimethylsilanediylbis(2-n-butyl-4-[4'-tert-butylphenyl]indenyl)zirconium dichloride, dimethylsilanediylbis(2-hexyl-4-[4'-tert-butylphenyl]indenyl)zirconium dichloride, dimethylsilanediyl(2-isopropyl-4-phenylindenyl)-2-methyl-4-phenylindenyl)zirconium dichloride, dimethylsilanediyl(2-isopropyl-4-(1-naphthyl)indenyl)-(2-methyl-4-(1-naphthyl) indenyl)zirconium dichloride, dimethylsilanediyl(2-isopropyl-4-[4'-tert-butylphenyl]indenyl)(2-methyl-4-[4'-tert-butylphenyl]indenyl)zirconium dichloride, dimethylsilanediyl(2-isopropyl-4-[4'-tert-butylphenyl]indenyl)-(2-ethyl-4-[4'-tert-butylphenyl]indenyl)zirconium dichloride, dimethylsilanediyl(2-isopropyl-4-[4'-tert-butylphenyl]indenyl)(2-methyl-4-[3',5'-bis-tert-butylphenyl] indenyl)zirconium dichloride, dimethylsilanediyl(2-isopropyl-4-[4'-tert-butylphenyl]indenyl)-2-methyl-4-[1'-naphthyl]indenyl)zirconium dichloride and ethylene(2-isopropyl-4-[4'-tert-butylphenyl]indenyl)-(2-methyl-4-[4'-tert-butylphenyl]indenyl)zirconium dichloride, and also the corresponding dimethylzirconium, monochloromono(alkylaryloxy)zirconium and di(alkylaryloxy)zirconium compounds. The complexes are preferably used in the rac form.

Such complexes can be synthesized by methods known per se, preferably by reacting the appropriately substituted, cyclic hydrocarbon anions with halides of titanium, zirconium, hafnium, vanadium, niobium, tantalum or chromium. Examples of appropriate preparative methods are described, inter alia, in Journal of Organometallic Chemistry, 369 (1989), 359-370.

Particularly useful compounds of the formula (XIVd) are those in which $M^{1D}$ is titanium or zirconium, in particular titanium, and $X^D$ is chlorine, $C_1$-$C_4$-alkyl or phenyl or two radicals $X^D$ form a substituted or unsubstituted butadiene ligand, $R^{15D}$ is

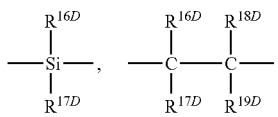

or $=BR^{16D}$ or $=BNR^{16D}R^{17D}$,
$A^{1D}$ is —O—, —S— or

t is 1 or 2, preferably 2,
$R^{1D}$ to $R^{3D}$ and $R^{5D}$ are each hydrogen, $C_1$-$C_{10}$-alkyl, preferably methyl, $C_3$-$C_{10}$-cycloalkyl, $C_6$-$C_{15}$-aryl $NR^{8D}_2$ or $Si(R^{8D})_3$, or two adjacent radicals form a cyclic group having from 4 to 12 carbon atoms, with particular preference being given to all $R^{1D}$ to $R^{3D}$ and $R^{5D}$ being methyl.

Particularly useful complexes D) of the formula (XIVd) are dimethylsilanediyl(tetramethylcyclopentadienyl)(phenylamino)titanium dichloride, dimethylsilanediyl(tetramethylcyclopentadienyl)(benzylamino)titanium dichloride, dimethylsilanediyl(tetramethylcyclopentadienyl)(tert-butylamino)titanium dichloride, dimethylsilanediyl(tetramethylcyclopentadienyl)(adamantyl)titanium dichloride and dimethylsilanediyl(indenyl)(tert-butylamino)titanium dichloride.

Another group of compounds of the formula (XIVd) which are particularly useful are those in which
$M^{1D}$ is titanium, vanadium or chromium, preferably in the oxidation state III, and
$X^D$ is chlorine, $C_1$-$C_4$-alkyl or phenyl or two radicals $X^D$ form a substituted or unsubstituted butadiene ligand,
$R^{15D}$ is

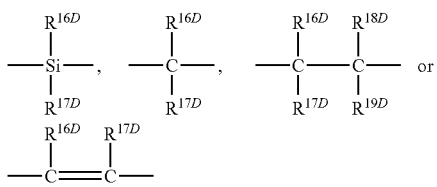

$A^{1D}$ is —O—$R^{22D}$, —$NR^{22D}_2$, —$PR^{22D}_2$ or an unsubstituted, substituted or fused, heterocyclic, in particular heteroaromatic, ring system,
v is 1 or when $A^{1D}$ is an unsubstituted, substituted or fused, heterocyclic ring system may be 0 or 1 and
$R^{1D}$ to $R^{3D}$ and $R^{5D}$ are each hydrogen, $C_1$-$C_{10}$-alkyl, $C_3$-$C_{10}$-cycloalkyl, $C_6$-$C_{15}$-aryl or $Si(R^{8D})_3$, or two adjacent radicals form a cyclic group having from 4 to 12 carbon atoms.

In a preferred embodiment, $A^{1D}$ is an unsubstituted, substituted or fused, heteroaromatic ring system and $M^{1D}$ is chromium. Very particular preference is given to $A^{1D}$ being an unsubstituted or substituted, e.g. alkyl-substituted, quinolyl or pyridyl bound in particular in position 2 or 8, whereas for the latter v is particularly preferable 0, e.g. 8-quinolyl, 8-(2-methylquinolyl), 8-(2,3,4-trimethylquinolyl), 8-(2,3,4,5,6,7-hexamethylquinolyl), v being 0 and $M^{1D}$ being chromium. Preferred catalysts D) of this type are 1-(8-quinolyl)-2-methyl-4-methylcyclopentadienylchromium(III) dichloride, 1-(8-quinolyl)-3-isopropyl-5-methylcyclopentadienylchromium(III) dichloride, 1-(8-quinolyl)-3-tert-butyl-5-methyl-cyclopentadienylchromium(III) dichloride, 1-(8-quinolyl)-2,3,4,5-tetramethylcyclopentadienylchromium(III) dichloride, 1-(8-quinolyl)tetrahydroindenylchromium(III) dichloride, 1-(8-quinolyl)indenylchromium(III) dichloride, 1-(8-quinolyl)-2-methylindenylchromium(III) dichloride, 1-(8-quinolyl)-2-isopropylindenylchromium(III) dichloride, 1-(8-quinolyl)-2-ethylindenylchromium(III) dichloride, 1-(8-quinolyl)-2-tert-butylindenylchromium(III) dichloride, 1-(8-quinolyl)benzindenylchromium(III) dichloride, 1-(8-quinolyl)-2-methylbenzindenylchromium(III) dichloride, 1-(8-(2-methylquinolyl))-2-methyl-4-methylcyclopentadienylchromium(III) dichloride, 1-(8-(2-methylquinolyl)-2,3,4,5-tetramethylcyclopentadienylchromium(III) dichloride, 1-(8-(2-methylquinolyl))tetrahydroindenylchromium(III) dichloride, 1-(8-(2-methylquinolyl))indenylchromium(III) dichloride, 1-(8-(2-methylquinolyl))-2-methylindenylchromium(III) dichloride, 1-(8-(2-methylquinolyl))-2-isopropylindenylchromium(III) dichloride, 1-(8-(2-methylquinolyl))-2-ethylindenylchromium(III) dichloride, 1-(8-(2-methylquinolyl))-2-tert-butylindenylchromium(III) dichloride, 1-(8-(2-methylquinolyl))benzindenylchromium (III) dichloride, 1-(2-pyridylmethyl)indenylchromium(III) dichloride or 1-(8-(2-methylquinolyl))-2-methylbenzindenylchromium(III) dichloride.

Furthermore, owing to the ease of preparation, preference is given to compounds in which $R^{15D}$ is CH=CH or 1,2-phenylene and $A^{1D}$ is $NR^{22D}_2$, and compounds in which $R^{15D}$ is $CH_2$, $C(CH_3)_2$ or $Si(CH_3)_2$ and $A^{1D}$ is unsubstituted or substituted 2- or 8-quinolyl or unsubstituted or substituted 2-pyridyl.

The preparation of such functional cyclopentadienyl ligands has been known for a long time. Various synthetic routes to these complexing ligands are described, for example, by M. Enders et al. in Chem. Ber. (1996), 129, 459-463, or P. Jutzi and U. Siemeling in J. Orgmet. Chem. (1995), 500, 175-185.

The metal complexes, in particular the chromium complexes, can be obtained in a simple manner by reacting the appropriate metal salts, e.g. metal chlorides, with the ligand anion (e.g. using methods analogous to the examples in DE-A-19710615).

Further suitable catalysts D) include metallocenes having at least one ligand which is formed from a cyclopentadienyl or heterocyclopentadienyl and a fused-on heterocycle, with the heterocycles preferably being aromatic and containing nitrogen and/or sulfur. Such compounds are described, for example, in WO 98/22486. These are in particular dimethylsilanediyl(2-methyl-4-phenylindenyl)(2,5-dimethyl-N-phenyl-4-azapentalene)zirconium dichloride, dimethylsilanediylbis(2-methyl-4-phenyl-4-hydroazulenyl)zirconium dichloride, dimethylsilanediylbis(2-ethyl-4-phenyl-4-hydroazulenyl)zirconium dichloride, bis(2,5-dimethyl-N-phenyl-4-azapentalene)zirconium dichloride or (indenyl)(2,5-dimethyl-N-phenyl-4-azapentalene)zirconium dichloride.

Further suitable catalysts D) are systems in which a metallocene compound is combined with, for example, an inorganic oxide which has been treated with zirconium alkoxide and subsequently chlorinated, for example by means of carbon tetrachloride. The preparation of such systems is described, for example, in WO 01/41920.

Other suitable catalysts D) include imidochromium compounds in which chromium bears at least one imido group as structural feature. These compounds and their preparation are described, for example, in WO 01/09148.

Further suitable components D) include transition metal complexes with a tridentate macrocyclic ligand, in particular substituted and unsubstituted 1,3,5-triazacyclohexanes and 1,4,7-triazacyclononanes. In the case of this type of catalyst, preference is likewise given to chromium complexes. Preferred catalysts of this type are [1,3,5-tri(methyl)-1,3,5-triazacyclohexane]chromium trichloride, [1,3,5-tri(ethyl)-1,3,5-triazacyclohexane]chromium trichloride, [1,3,5-tri(octyl)-1,3,5-triazacyclohexane]chromium trichloride, [1,3,5-tri(dodecyl)-1,3,5-triazacyclohexane]chromium trichloride and [1,3,5-tri(benzyl)-1,3,5-triazacyclohexane]chromium trichloride.

Further suitable catalysts D) are, for example, transition metal complexes with at least one ligand of the formulae XV to XIX,

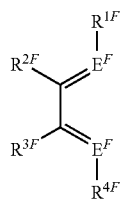

XV

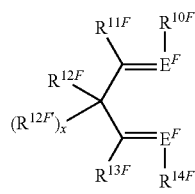

XVI

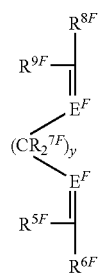

XVII

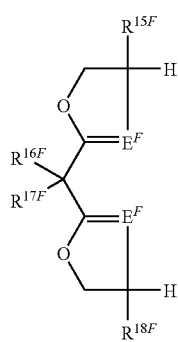

XVIII

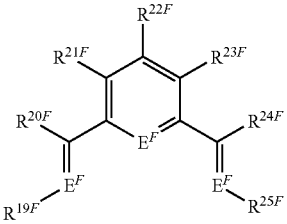

XIX where the transition metal is selected from among the elements Ti, Zr, Hf, Sc, V, Nb, Ta, Cr, Mo, W, Fe, Co, Ni, Pd, Pt and the elements of the rare earth metals. Preference is given to compounds having nickel, iron, cobalt or palladium as central metal.

$E^F$ is an element of group 15 of the Periodic Table of the Elements, preferably N or P, with particular preference being given to N. The two or three atoms $E^F$ in a molecule can be identical or different.

The radicals $R^{1F}$ to $R^{25F}$, which may be identical or different within a ligand system XV to XIX, are as follows:

$R^{1F}$ and $R^{4F}$ are each, independently of one another, a hydrocarbon radical or a substituted hydrocarbon radical, preferably a hydrocarbon radical in which the carbon atom adjacent to the element $E^F$ is bound to at least two carbon atoms;

$R^{2F}$ and $R^{3F}$ are each, independently of one another, hydrogen, a hydrocarbon radical or a substituted hydrocarbon radical, where $R^{2F}$ and $R^{3F}$ may together also form a ring system in which one or more heteroatoms may be present, $R^{6F}$ and $R^{8F}$ are each, independently of one another, a hydrocarbon radical or a substituted hydrocarbon radical, $R^{5F}$ and $R^{9F}$ are each, independently of one another, hydrogen, a hydrocarbon radical or a substituted hydrocarbon radical, where $R^{6F}$ and $R^{5F}$ or $R^{8F}$ and $R^{9F}$ may together also form a ring system, the radicals $R^{7F}$ are each, independently of one another, hydrogen, a hydrocarbon radical or a substituted hydrocarbon radical, where two radicals $R^{7F}$ may together also form a ring system, $R^{10F}$ and $R^{14F}$ are each, independently of one another, a hydrocarbon radical or a substituted hydrocarbon radical, $R^{11F}$, $R^{12F}$, $R^{12F'}$ and $R^{13F}$ are each, independently of one another, hydrogen, a hydrocarbon radical or a substituted hydrocarbon radical, where two or more geminal or vicinal radicals $R^{11A}$, $R^{12A}$, $R^{12A'}$ and $R^{13A}$ may together also form a ring system, $R^{15F}$ and $R^{18F}$ are each, independently of one another, hydrogen, a hydrocarbon radical or a substituted hydrocarbon radical, $R^{16F}$ and $R^{17F}$ are each, independently of one another, hydrogen, a hydrocarbon radical or a substituted hydrocarbon radical, $R^{19F}$ and $R^{25F}$ are each, independently of one another, $C_2$-$C_{20}$-alkenyl, $C_6$-$C_{20}$-aryl, arylalkyl having from 1 to 10 carbon atoms in the alkyl part and 6-20 carbon atoms in the aryl part, where the organic radicals $R^{19F}$ and $R^{25F}$ may also be substituted by halogens, $R^{20F}$-$R^{24F}$ are each, independently of one another, hydrogen, $C_1$-$C_{20}$-alkyl, $C_2$-$C_{20}$-alkenyl, $C_6$-$C_{20}$-aryl, arylalkyl having from 1 to 10 carbon atoms in the alkyl part and 6-20 carbon atoms in the aryl part or $SiR^{26F}_3$, where the organic radicals $R^{20F}$-$R^{24F}$ may also be substituted by halogens and two vicinal radicals $R^{20F}$-$R^{24F}$ may also be joined to form a five- or six-membered ring and the radicals $R^{26F}$ are each, independently of one another, hydrogen, $C_1$-$C_{20}$-alkyl, $C_2$-$C_{20}$-alkenyl, $C_6$-$C_{20}$-aryl or arylalkyl having from 1 to 10 carbon atoms in the alkyl part and 6-20 carbon atoms in the aryl part and two radicals $R^{26F}$ may also be joined to form a five- or six-membered ring.

x is 0 or 1, with the complex of the formula (XVI) being negatively charged when x=0, and y is an integer from 1 to 4, preferably 2 or 3.

Particularly useful transition metal complexes are those having Fe, Co, Ni, Pd or Pt as central metal and containing ligands of the formula (XV). Particular preference is given to diimine complexes of Ni or Pd, e.g.:

di(2,6-di-i-propylphenyl)-2,3-dimethyldiazabutadiene-palladium dichloride, di(di-i-propylphenyl)-2,3-dimethyldiazabutadienenickel dichloride, di(2,6-di-i-propylphenyl) dimethyldiazabutadienedimethylpalladium, di(2,6-di-i-propylphenyl)-2,3-dimethyldiazabutadienedimethylnickel, di(2,6-dimethylphenyl)-2,3-dimethyldiazabutadienepalladium dichloride, di(2,6-dimethylphenyl)-2,3-dimethyldiazabutadienenickel dichloride, di(2,6-dimethylphenyl)-2,3-dimethyldiazabutadienedimethylpalladium, di(2,6-dimethylphenyl)-2,3-dimethyldiazabutadienedimethylnickel, di(2-methylphenyl)-2,3-dimethyldiazabutadienepalladium dichloride, di(2-methylphenyl)-2,3-dimethyldiazabutadienenickel dichloride, di(2-methylphenyl)-2,3-dimethyldiazabutadienedimethylpalladium, di(2-methylphenyl)-2,3-dimethyldiazabutadienedimethylnickel, diphenyl-2,3-dimethyldiazabutadienepalladium dichloride, diphenyl-2,3-dimethyldiazabutadienenickel dichloride, diphenyl-2,3-dimethyldiazabutadienedimethylpalladium, diphenyl-2,3-dimethyldiazabutadienedimethylnickel, di(2,6-dimethylphenyl)azanaphthenepalladium dichloride, di(2,6-dimethylphenyl)azanaphthenenickel dichloride, di(2,6-dimethylphenyl)azanaphthenedimethylpalladium, di(2,6-dimethylphenyl)azanaphthenedimethylnickel, 1,1'-bipyridylpalladium dichloride, 1,1'-bipyridylnickel dichloride, 1,1'-bipyridyl(dimethyl)palladium, 1,1'-bipyridyl(dimethyl)nickel.

Particularly useful compounds (XIX) also include those which are described in J. Am. Chem. Soc. 120, p. 4049 ff. (1998), J. Chem. Soc., Commun. 1998, 849, and WO 98/27124. $E^F$ is preferably nitrogen and $R^{19F}$ and $R^{25F}$ in (XIX) are preferably phenyl, naphthyl, biphenyl, anthranyl, o-, m-, p-methylphenyl, 2,3-, 2,4-, 2,5- or 2,6-dimethylphenyl, -dichlorophenyl or -dibromophenyl, 2-chloro-6-methylphenyl, 2,3,4-, 2,3,5-, 2,3,6-, 2,4,5-, 2,4,6- or 3,4,5-trimethylphenyl, in particular 2,3- or 2,6-dimethylphenyl, -diisopropylphenyl, -dichlorophenyl or -dibromophenyl and 2,4,6-trimethylphenyl. At the same time, $R^{20F}$ and $R^{24F}$ are preferably hydrogen, methyl, ethyl, n-propyl, isopropyl, n-butyl, tert-butyl, n-pentyl, n-hexyl, n-heptyl, n-octyl, benzyl or phenyl, in particular hydrogen or methyl. $R^{21F}$ and $R^{23F}$ are preferably hydrogen and $R^{22F}$ is preferably hydrogen, methyl, ethyl or phenyl, in particular hydrogen. Preference is given to complexes of the ligands XIX with the transition metals Fe, Co or Ni, in particular Fe. Particular preference is given to 2,6-diacetylpyridinebis(2,4-dimethylphenylimine) iron dichloride, 2,6-diacetylpyridinebis(2,4,6-trimethylphenylimine)iron dichloride, 2,6-diacetylpyridinebis(2-chloro-6-methylphenylimine)iron dichloride, 2,6-diacetylpyridinebis(2,6-diisopropylphenylimine)iron dichloride, 2,6-diacetylpyridinebis(2,6-dichlorophenylimine)iron dichloride, 2,6-pyridinedicarboxaldehydebis(2,6-diisopropylphenylimine)iron dichloride, 2,6-diacetylpyridinebis(2,4-dimethylphenylimine)cobalt dichloride, 2,6-diacetylpyridinebis(2,4,6-trimethylphenylimine)cobalt dichloride, 2,6-diacetylpyridinebis(2-chloro-6-methylphenylimine)cobalt dichloride, 2,6-diacetylpyridinebis(2,6-diisopropylphenylimine)cobalt dichloride, 2,6-diacetylpyridinebis(2,6-dichlorophenylimine)cobalt dichloride, and 2,6-pyridinedicarboxaldehydebis(2,6-diisopropylphenylimine)cobalt dichloride.

Iminophenoxide complexes can also be used as catalysts D). The ligands of these complexes can be prepared, for example, from substituted or unsubstituted salicylaldehydes and primary amines, in particular substituted or unsubstituted arylamines. Transition metal complexes with pi ligands having one or more heteroatoms in the pi system, for example the boratabenzene ligand, the pyrrolyl anion or the phospholyl anion, can also be used as catalysts D).

Further complexes suitable as catalysts D) include those which have bidentate or tridentate chelating ligands. In such ligands, for example, an ether function is linked to an amine or amide function or an amide is linked to a heteroaromatic such as pyridine.

Such combinations of components A) and D) enable, for example, bimodal products to be prepared or comonomers to be generated in situ. Preference is given to using at least one monocyclopentadienyl complex A) in the presence of at least one further catalyst D) customary for the polymerization of olefins and if desired, one or more activating compounds C). Here, depending on the catalyst combinations A) and D), one or more activating compounds C) may be advantageous. The polymerization catalysts D) can likewise be supported and can be used simultaneously or in any order with the complex A) of the present invention. For example, the monocyclopentadienyl complex A) and the polymerization catalysts D) can be applied together to a support B) or different supports B). It is also possible to use mixtures of various catalysts as component D). The molar ratio of transition metal complex A) to polymerization catalyst B) is usually in the range from 1:100 to 100:1, preferably from 1:10 to 20:1 and particularly preferably from 1:1 to 10:1.

The catalyst system may further comprise, as additional component E), a metal compound of the formula (XX),

$$M^G(R^{1G})_{r^G}(R^{2G})_{s^G}(R^{3G})_{t^G} \qquad (XX)$$

where $M^G$ is Li, Na, K, Be, Mg, Ca, Sr, Ba, boron, aluminum, gallium, indium, thallium, zinc, in particular Li, Na, K, Mg, boron, aluminum or Zn, $R^{1G}$ is hydrogen, $C_1$-$C_{10}$-alkyl, $C_6$-$C_{15}$-aryl, arylalkyl or arylalkyl each having from 1 to 10 carbon atoms in the alkyl part and from 6 to 20 carbon atoms in the aryl part, $R^{2G}$ and $R^{3G}$ are each hydrogen, halogen, $C_1$-$C_{10}$alkyl, $C_6$-$C_{15}$-aryl, arylalkyl, arylalkyl or alkoxy each having from 1 to 20 carbon atoms in the alkyl radical and from 6 to 20 carbon atoms in the aryl radical, or alkoxy with $C_1$-$C_{10}$-alkyl or $C_6$-$C_{15}$-aryl, $r^G$ is an integer from 1 to 3 and $s^G$ and $t^G$ are integers from 0 to 2, with the sum $r^G$+$s^G$+$t^G$ corresponding to the valence of $M^G$, where the component E) is not identical to the component C). It is also possible to use mixtures of various metal compounds of the formula (XX).

Among the metal compounds of the formula (XX), preference is given to those in which
$M^G$ is lithium, magnesium, boron or aluminum and
$R^{1G}$ is $C_1$-$C_{20}$-alkyl.

Particularly preferred metal compounds of the formula (XX) are methyllithium, ethyllithium, n-butyllithium, methylmagnesium chloride, methylmagnesium bromide, ethylmagnesium chloride, ethylmagnesium bromide, butylmagnesium chloride, dimethylmagnesium, diethylmagnesium, dibutylmagnesium, n-butyl-n-octylmagnesium, n-butyl-n-heptylmagnesium, in particular n-butyl-n-octylmagnesium, tri-n-hexylaluminum, triisobutylaluminum, tri-n-butylaluminum, triethylaluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum alkyls with alcohols can also be used.

When a metal compound E) is used, it is preferably present in the catalyst system in such an amount that the molar ratio of $M^G$ from formula (XX) to transition metal from monocyclopentadienyl compound A) is from 2 000:1 to 0.1:1, preferably from 800:1 to 0.2:1 and particularly preferably from 100:1 to 1:1.

In general, the catalyst solid together with the further metal compound E) of the formula (XX), which may be different from the metal compound or compounds E) used in the preparation of the catalyst solid, is used as constituent of a catalyst system for the polymerization or copolymerization of olefins. It is also possible, particularly when the catalyst solid does not contain any activating component C), for the catalyst system to further comprise, in addition to the catalyst solid, one or more activating compounds C) which are identical to or different from any activating compounds C) present in the catalyst solid.

To prepare the catalyst systems of the present invention, preference is given to immobilizing at least one of the components A) and/or C) on the support B) by physisorption or by means of chemical reaction, i.e. covalent binding of the components, with reactive groups of the support surface. The order in which the support component B), the component A) and any component C) are combined is immaterial. The components A) and C) can be added independently of one another or simultaneously or in premixed form to B). After the individual process steps, the solid can be washed with suitable inert solvents such as aliphatic or aromatic hydrocarbons.

In a preferred embodiment, the monocyclopentadienyl complex A) is brought into contact with the activating compound C) in a suitable solvent, usually giving a soluble reaction product, an adduct or a mixture. The preparation obtained in this way is then brought into contact with the support B), which may have been pretreated, and the solvent is completely or partly removed. This preferably gives a solid in the form of a free-flowing powder. Examples of the industrial implementation of the above process are described in WO 96/00243, WO 98/40419 or WO 00/05277. A further preferred embodiment comprises firstly applying the activating compound C) to the support B) and subsequently bringing this supported activating compound into contact with the monocyclopentadienyl complex A).

The component D) can likewise be reacted in any order with the components A) and, if desired, B), C) and E). Preference is given to bringing D) firstly into contact with component C) and then dealing with the components A) and B) and any further C) as described above. In another preferred embodiment, a catalyst solid is prepared from the components A), B) and C) as described above and this is brought into contact with the component E) during, at the beginning of or shortly before the polymerization. Preference is given to E) firstly being brought into contact with the α-olefin to be polymerized and the catalyst solid comprising the components A), B) and C) as described above subsequently being added.

The monocyclopentadienyl complex A) can be brought into contact with the component(s) C) and/or D) either before or after being brought into contact with the olefin to be polymerized. Preactivation using one or more components C) prior to mixing with the olefin and further addition of the same or different components C) and/or D) after the mixture has been brought into contact with the olefin is also possible. Preactivation is generally carried out at 10-100° C., in particular 20-80° C.

It is also possible for the catalyst system firstly to be prepolymerized with α-olefins, preferably linear $C_2$-$C_{10}$-1-alkenes and in particular ethylene or propylene, and the resulting prepolymerized catalyst solid then to be used in the actual polymerization. The mass ratio of catalyst solid used in the prepolymerization to monomer polymerized onto it is usually in the range from 1:0.1 to 1:1 000, preferably from 1:1 to 1:200.

Furthermore, a small amount of an olefin, preferably an α-olefin, for example vinylcyclohexane, styrene or phenyldimethylvinylsilane, as modifying component, an antistatic or a suitable inert compound such as a wax or oil can be added as additive during or after the preparation of the catalyst system. The molar ratio of additives to transition metal compound B) is usually from 1:1 000 to 1 000:1, preferably from 1:5 to 20:1.

The catalyst systems of the present invention are suitable for the polymerization of olefins and especially for the polymerization of α-olefins, i.e. hydrocarbons having terminal double bonds. Suitable monomers also include functionalized olefinically unsaturated compounds such as acrolein, ester or amide derivatives of acrylic or methacrylic acid, for example acrylates, methacrylates or acrylonitrile, or vinyl esters, for example vinyl acetate. Preference is given to nonpolar olefinic compounds, including aryl-substituted α-olefins. Particularly preferred α-olefins are linear or branched $C_2$-$C_{12}$-1-alkenes, in particular linear $C_2$-$C_{10}$-1-alkenes such as ethene, propene, 1-butene, 1-pentene, 1-hexene, 1-heptene, 1-octene, 1-decene or branched $C_2$-$C_{10}$-1-alkenes such as 4-methyl-1-pentene, conjugated and unconjugated dienes such as 1,3-butadiene, 1,5-hexadiene or 1,7-octadiene or vinylaromatic compounds such as styrene or substituted styrene. It is also possible to polymerize mixtures of various α-olefins. Preference is given to polymerizing at least one olefin selected from the group consisting of ethene, propene, 1-butene, 1-pentene, 1-hexene, 1-heptene, 1-octene and 1-decene.

Suitable olefins also include ones in which the double bond is part of a cyclic structure which can have one or more ring systems. Examples are cyclopentene, cyclohexene, norbornene, tetracyclododecene and methylnorbornene and dienes such as 5-ethylidene-2-norbornene, norbornadiene or ethylnorbornadiene.

Mixtures of two or more olefins can also be polymerized. In contrast to some known iron and cobalt complexes, the transition metal complexes of the present invention display a good polymerization activity even in the case of higher α-olefins, so that their suitability for copolymerization deserves particular emphasis. In particular, the transition metal complexes of the present invention can be used for the polymerization or copolymerization of ethene or propene. As comonomers in the polymerization of ethene, preference is given to using $C_3$-$C_8$-α-olefins or norbornene, in particular 1-butene, 1-pentene, 1-hexene and/or 1-octene. Preference is given to using monomer mixtures containing at least 50 mol % of ethene. Preferred comonomers in the polymerization of propylene are ethene and/or butene.

The polymerization can be carried out in a known manner in bulk, in suspension, in the gas phase or in a supercritical medium in the customary reactors used for the polymerization of olefins. It can be carried out batchwise or preferably continuously in one or more stages. High-pressure polymerization processes in tube reactors or autoclaves, solution processes, suspension processes, stirred gas-phase processes or gas-phase fluidized-bed processes are all possible.

The polymerizations are usually carried out at from −60 to 350° C. under pressures of from 0.5 to 4 000 bar at mean residence times of from 0.5 to 5 hours, preferably from 0.5 to 3 hours. The advantageous pressure and temperature ranges for carrying out the polymerizations usually depend on the polymerization method. In the case of high-pressure polymerization processes, which are usually carried out at pressures of from 1 000 to 4 000 bar, in particular from 2 000 to 3 500 bar, high polymerization temperatures are generally also set. Advantageous temperature ranges for these high-pressure polymerization processes are from 200 to 320° C., in particular from 220 to 290° C. In the case of low-pressure polymerization processes, a temperature which is at least a few degrees below the softening temperature of the polymer is generally set. These polymerization processes are preferably carried out at from 50 to 180° C., preferably from 70 to 120° C. In the case of suspension polymerization, the polymerization is usually carried out in a suspension medium, preferably an inert hydrocarbon such as isobutane or a mixture of hydrocarbons, or else in the monomers themselves. The polymerization temperatures are generally in the range from −20 to 115° C., and the pressure is generally in the range from 1 to 100 bar. The solids content of the suspension is generally in the range from 10 to 80%. The polymerization can be carried out batchwise, e.g. in stirring autoclaves, or continuously, e.g. in tube reactors, preferably in loop reactors. Particular preference is given to employing the Phillips PF process as described in U.S. Pat. No. 3,242,150 and U.S. Pat. No. 3,248,179. The gas-phase polymerization is generally carried out at from 30 to 125° C.

Among the abovementioned polymerization processes, particular preference is given to gas-phase polymerization, in particular in gas-phase fluidized-bed reactors, solution polymerization and suspension polymerization, in particular in loop reactors and stirred tank reactors. The gas-phase polymerization can also be carried out in the condensed or supercondensed phase, in which part of the circulating gas is cooled to below the dew point and is recirculated as a two-phase mixture to the reactor. It is also possible to use a multizone reactor in which two polymerization zones are linked to one another and the polymer is passed alternately through these two zones a number of times. The two zones can also have different polymerization conditions. Such a reactor is described, for example, in WO 97/04015. The different or identical polymerization processes can also, if desired, be connected in series so as to form a polymerization cascade, for example in the Hostalen process. A parallel reactor arrangement using two or more identical or different processes is also possible. Furthermore, molar mass regulators, for example hydrogen, or customary additives such as antistatics can also be used in the polymerizations.

The monocyclopentadienyl complexes of the present invention and the catalyst systems in which they are present can also be prepared by means of combinatorial methods or their polymerization activity can be tested with the aid of these combinatorial methods, often referred to as high throughput screening.

The process of the present invention allows polymers of olefins to be prepared. The term "polymerization" as used here in the description of the present invention encompasses both polymerization and oligomerization, i.e. oligomers and polymers having molar masses $M_w$ in the range from about 56 to 10 000 000 can be produced by this process.

Owing to their good mechanical properties, the olefin polymers prepared using the catalyst system of the present invention are particularly useful for the production of films, fibers and moldings.

The catalyst systems of the present invention give polymers having molar masses which are lower than those obtained using catalyst systems having $C_2$ bridges. Even when ethylene is polymerized without further comonomers, the use of the catalysts of the present invention results in ethylene polymers having a high degree of branching. In addition, the catalyst systems of the present invention can be prepared in a simple fashion and in high yields.

EXAMPLES

All syntheses and polymerizations were carried out under a protective nitrogen atmosphere.

The density [g/cm$^3$] was determined in accordance with ISO 1183.

The Staudinger index (η)[dl/g] was determined by means of an automatic Ubbelohde viscometer (Lauda PVS 1) using decalin as solvent at 130° C. (ISO 1628 at 130° C., 0.001 g/ml of decalin).

The NMR spectra were measured on a Bruker DRX 200 ($^1$H: 200.13 MHz). The signal of the incompletely deuterated part of the solvent used served as internal standard in $^1$H-NMR spectra. All signals were calibrated to the corresponding literature values.

Mass spectra were recorded on a Finnigan MAT 8230, and high-resolution mass spectra were measured on a Micromass CTD ZAB-2F VH spectrometer.

Abbreviations in the following tables:

Cat. Catalyst
t(poly) polymerization time
Polymer amount of polymer formed
Density polymer density
Prod. Productivity of the catalyst in g of polymer obtained per mmol of catalyst used (chromium complex) per hour
Hexene whether or not hexene is present during the polymerization Example 1

1.1. Preparation of 1-chlorodimethylsilyl-2,3,4,5-tetramethylcyclopentadiene

A solution of 16 mmol of 2,3,4,5-tetramethylcyclopentadienyllithium in 100 ml of tetrahydrofuran was cooled to −40° C. and subsequently added while stirring to a solution of 3.16 g of dimethylsilyl dichloride (24 mmol) in 50 ml of tetrahydrofuran. The mixture was allowed to warm to room temperature while stirring and was stirred for a further 2 hours. The volatile components were then distilled off and the residue obtained in this way was extracted with hexane and filtered. The solvent was distilled off from the resulting filtrate. This gave 2.2 g (10.2 mmol, 43%) of 1-chlorodimethylsilyl-2,3,4,5-tetramethylcyclopentadiene.

NMR ¹H (200.13 MHz, CDCl₃): 0.72 (6H, s, CH₃—Si); 1.84 (9H, s, CH₃-Cp); 2.01 (3H, s, CH₃-Cp); 3.1 (1H, s, H-Cp)

1.2. Preparation of 1-(dimethyl(2-oxy-pyridine)silyl)-2,3,4,5-tetramethylcyclopentadiene A solution of 0.97 g (10.2 mmol) of 2-hydroxypyridine and 1.07 g (10.5 mmol) of triethylamine in 50 ml of toluene was cooled to −50° C. and subsequently added while stirring to 2.2 g (10.2 mmol) of 1-chlorodimethylsilyl-2,3,4,5-tetramethylcyclopentadiene in 25 ml of toluene. The mixture was allowed to warm to room temperature while stirring and was stirred for a further 12 hours. The solvent was then distilled off and the residue obtained in this way was distilled at 25 mbar/100° C. This gave 1.84 g (6.7 mmol, 66% yield) of 1-dimethyl(2-oxypyridine)silyl)-2,3,4,5-tetramethylcyclopentadiene.

NMR ¹H (200.13 MHz, CDCl₃): 0.14 (6H, s, CH₃—Si); 1.69-1.93 (12H, m, CH₃-Cp); 2.66 (1H, s, H-Cp); 6.26 (1H, t, Py-H); 6.58 (1H, d, Py-H); 7.23-7.79 (2H, m, Py-H).

1.3. Preparation of (1-(dimethyl(2-oxypyridine)silyl)-2,3,4,5-tetramethylcyclopentadiene)chromium dichloride

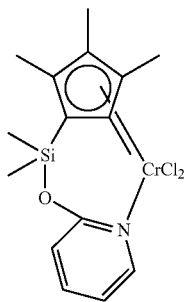

A solution of 0.58 g (2.12 mmol) of 1-(dimethyl(2-oxypyridine)silyl)-2,3,4,5-tetramethylcyclopentadiene in 20 ml of tetrahydrofuran was cooled to 80° C. and subsequently added to n-butyllithium (2.5 M in hexane, 2.12 mmol). After stirring at this temperature for 20 minutes, the reaction mixture was added while stirring to a solution of 0.335 g (2.12 mmol) of chromium trichloride tris(tetrahydrofuran) in 30 ml of tetrahydrofuran. The mixture was stirred for a further 12 hours at room temperature, and the solvent was then distilled off and the residue washed with hexane. The soluble part of the residue obtained in this way was taken up in toluene and filtered. The filtrate was freed of solvent and dried under reduced pressure. This gave (1-(dimethyl(2-oxypyridine)silyl)-2,3,4,5-tetramethylcyclopentadienyl)chromium dichloride.

MS (EI), m/e (%): 359.2 (M⁺-HCl, 100).

Example 2

2.1. Preparation of 1-chlorodimethylsilylcyclopentadiene

A solution of 30 mmol of cyclopentadienyllithium in 50 ml of tetrahydrofuran was cooled to −40° C. and subsequently added while stirring to a solution of 3.9 g of dimethylsilyl dichloride (30 mmol) in 50 ml of tetrahydrofuran. The mixture was allowed to warm to room temperature while stirring and was stirred for a further 2 hours. The volatile components were then distilled off and the residue obtained in this way was extracted with hexane and filtered. The solvent was distilled off from the resulting filtrate and the residue was distilled at 60° C./27 mbar. This gave 2.17 g (13.7 mmol, 46%) of 1-chlorodimethylsilylcyclopentadiene.

NMR ¹H (200.13 MHz, CDCl₃): 0.26 (6H, s, CH₃—Si); 3.13 (1H, t, H-Cp); 6.53-6.7 (4H, m, H-Cp).

2.2. Preparation of 1-dimethyl(2-oxypyridine)silyl)cyclopentadiene

A solution of 1.23 g (13.7 mmol) of 2-hydroxypyridine and 2.52 g (25 mmol) of triethylamine in 50 ml of toluene was cooled to −50° C. and subsequently added while stirring to 2.17 g (13.7 mmol) of 1-chlorodimethylsilylcyclopentadiene in 25 ml of toluene. The mixture was allowed to warm to room temperature while stirring and was stirred for a further 12 hours. The solvent was then distilled off and the residue obtained in this way was distilled at 26 mbar/50° C. This gave 0.97 g (4.4 mmol, 34% yield) of 1-(dimethyl(2-oxypyridine)silyl)cyclopentadiene.

NMR ¹H (200.13 MHz, CDCl₃): −0.08-0.51 (6H, s, CH₃—Si); 3.18 (1H, t, H-Cp); 6.26-6.88 (4H, m, H-Cp); 7.23-8.09 (4H, m, Py-H).

2.3. Preparation of (1-(dimethyl(2-oxypyridine)silyl)cyclopentadienyl)chromium dichloride

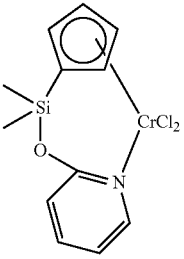

0.19 g of potassium hydride (4.4 mmol) was added to a solution of 0.97 g (4.4 mmol) of 1-(dimethyl(2-oxypyridine)silyl)cyclopentadiene in 20 ml of tetrahydrofuran. After stirring at room temperature for 2 hours, the reaction mixture was added while stirring to a solution of 0.689 g (4.4 mmol) of chromium trichloride tris(tetrahydrofuran) in 50 ml of tetrahydrofuran. The mixture was stirred at room temperature for a further 12 hours, and the solvent was then distilled off and the residue washed with hexane. The soluble part of the residue obtained in this way was taken up in toluene and filtered. The filtrate was freed of solvent and dried under reduced pressure. This gave 0.385 g of (1-(dimethyl(2-oxypyridine)silyl)cyclopentadienyl)chromium dichloride.

MS (EI), m/e (%): 338.1 (M⁺, 49).

Example 3

3.1. Preparation of 1-chlorodiisopropylsilylcyclopentadiene

A solution of 4.32 g (49.05 mmol) of cyclopentadienylsodium in 200 ml of tetrahydrofuran was cooled to −50° C. and subsequently added while stirring to 9.13 g of diisopropylsilyl dichloride (49.05 mmol). The mixture was allowed to warm to room temperature while stirring and was stirred for a further 12 hours. The solvent was then distilled off and the residue obtained in this way was extracted with hexane and filtered. The solvent was distilled off from the resulting filtrate. This gave 9.2 g (42.95 mmol, 88%) of 1-chlorodiisopropylsilylcyclopentadiene.

NMR $^1$H (200.13 MHz, CDCl$_3$): 0.69-1.27 (m, C$\underline{H_3}$,C$\underline{H}$-iPr); 2.9 (s, C$\underline{H_2}$-Cp); 6.37-7.01 ($\underline{H}$-Cp)

MS (EI), m/e (%): 214 (M$^+$, 70): 171 (M$^+$-iPr, 100); 143 (M$^+$-Cl$_2$, 98).

3.2. Preparation of 1-(diisopropyl(2-oxypyridine)silyl)cyclopentadiene

A solution of 2 g (21.02 mmol) of 2-hydroxypyridine and 2.4 g (23.74 mmol) of triethylamine in 100 ml of toluene was cooled to −60° C. and subsequently added while stirring to 4.5 g (21.02 mmol) of 1-chlorodiisopropylsilylcyclopentadiene in 50 ml of tetrahydrofuran. The mixture was allowed to warm to room temperature while stirring and was stirred for a further 12 hours. The solvent was then distilled off and the residue obtained in this way was extracted with hexane and filtered. The solvent was distilled off from the resulting filtrate. This gave 5.2 g (18.95 mmol, 90% yield) of 1-(diisopropyl(2-oxypyridine)silyl)cyclopentadiene.

NMR $^1$H (200.13 MHz, CDCl$_3$): 0.95-1.32 (m, C$\underline{H_3}$,C$\underline{H}$-iPr); 3.19 (s, C$\underline{H_2}$-Cp); 6.27-8.10 ($\underline{H}$-Cp, $\underline{H}$-Py).

MS (EI), m/e (%): 273 (M$^+$, 20); 230 (M$^+$-iPr, 100).

3.3. Preparation of 1-(diisopropyl(2-oxypyridine)silyl)cyclopentadienyl)chromium dichloride

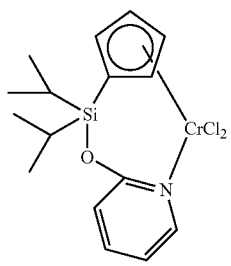

A solution of 1.49 g (5.45 mmol) of 1-(diisopropyl(2-oxypyridine)silyl)cyclopentadiene in 40 ml of tetrahydrofuran was cooled to −60° C. and subsequently added to 3.6 ml of tert-butyllithium (1.5 M in hexane, 5.45 mmol). After stirring at this temperature for 30 minutes, the mixture was allowed to warm to room temperature while stirring and was stirred for a further 4 hours. The reaction mixture was subsequently added while stirring to a solution of 2.52 g (6.73 mmol) of chromium trichloride tris(tetrahydrofuran) in 50 ml of tetrahydrofuran. The mixture was stirred at room temperature for a further 12 hours, and the solvent was then distilled off and the residue was washed with hexane. The soluble part of the residue obtained in this way was taken up in toluene and filtered. The filtrate was freed of solvent and dried under reduced pressure. This gave 1.8 g (4.55 mmol) of 1-(diisopropyl(2-oxypyridine)silyl)cyclopentadienyl)chromium dichloride (83%).

NMR $^1$H (200.13 MHz, CDCl$_3$): −31 ($\underline{H}$-Py); 34 ($\underline{H}$-Py); 2 (C$\underline{H_3}$-iPr).

Example 4

4.1. Preparation of 1-chlorodiisopropylsilyl-3-methylcyclopentadiene

A solution of 0.8 g (9.34 mmol) of methylcyclopentadienyllithium in 100 ml of tetrahydrofuran was cooled to −50° C. and subsequently added while stirring to 1.7 ml of diisopropylsilyl dichloride (9.34 mmol). The mixture was allowed to warm to room temperature while stirring and was stirred for a further 12 hours. The solvent was then distilled off and the residue obtained in this way was extracted with hexane and filtered. The solvent was distilled off from the resulting filtrate. This gave 1.87 g (8.18 mmol, 88%) of 1-chlorodiisopropylsilyl-3-methylcyclopentadiene.

NMR $^1$H (200.13 MHz, CDCl$_3$): 0.80-1.2 (m, C$\underline{H_3}$,C$\underline{H}$-iPr); 1.69 (s, C$\underline{H_3}$-Cp); 2.99 (d, C$\underline{H_2}$-Cp); 6.10-6.94 ($\underline{H}$-Cp)

MS (EI), m/e (%): 228 (M$^+$, 70); 185 (M$^+$-iPr, 100); 157 (M$^+$-Cl$_2$, 98).

4.2. Preparation of 1-(diisopropyl(2-oxypyridine)silyl)-3-methylcyclopentadiene A solution of 0.8 g (8.36 mmol) of 2-hydroxypyridine and 1.2 g (11.86 mmol) of triethylamine in 100 ml of toluene was cooled to −60° C. and subsequently added while stirring to 1.87 g (8.18 mmol) of 1-chlorodiisopropylsilyl-3-methylcyclopentadiene in 50 ml of tetrahydrofuran. The mixture was allowed to warm to room temperature while stirring and was stirred for a further 12 hours. The solvent was then distilled off and the residue obtained in this way was extracted with hexane and filtered. The solvent was distilled off from the resulting filtrate. This gave 2.25 g (7.81 mmol, 95% yield) of 1-(diisopropyl(2-oxypyridine)silyl)-3-methylcyclopentadiene.

NMR $^1$H (200.13 MHz, CDCl$_3$): 1.00-1.40 (m, C$\underline{H_3}$, C$\underline{H}$-iPr); 2.10 (s, C$\underline{H_3}$-Cp); 3.09 (s, C$\underline{H_2}$-Cp); 6.11-8.05 ($\underline{H}$-Cp, $\underline{H}$-Py).

2.3. Preparation of 1-(diisopropyl(2-oxypyridine)silyl)-3-methylcyclopentadienyl)chromium dichloride

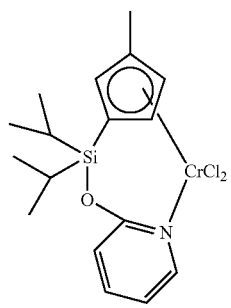

A solution of 0.94 g (3.3 mmol) of 1-(diisopropyl(2-oxypyridine)silyl)-3-methylcyclopentadiene in 40 ml of tetrahydrofuran was cooled to −60° C. and subsequently added to 2.2 ml of tertbutyllithium (1.5 M in hexane, 3.3 mmol). After stirring at this temperature for 30 minutes, the mixture was allowed to warm to room temperature while stirring and was stirred for a further 4 hours. The reaction mixture was subsequently added while stirring to a solution of 1.08 g (2.89 mmol) of chromium trichloride tris(tetrahydrofuran) in 50 ml of tetrahydrofuran. The mixture was stirred at room temperature for a further 12 hours, and the solvent was then distilled off and the residue washed with hexane. The soluble part of the residue obtained in this way was taken up in toluene and filtered. The filtrate was freed of solvent and dried under reduced pressure. This gave 0.73 g (1.77 mmol) of 1-(diisopropyl(2-oxypyridine)silyl)-3-methylcyclopentadienyl) chromium dichloride (61%).

NMR $^1$H (200.13 MHz, CDCl$_3$): −66 (C$\underline{H}_3$-Cp); −32 ( $\underline{H}$-Py); 33 ($\underline{H}$-Py); 2 (C$\underline{H}_3$-iPr).

Example 5 (Comparative Example)

1-(8-Quinolyl)-2,3,4,5-tetramethylcyclopentadienyl-chromium dichloride was prepared as described in U.S. Pat. No. 6,437,161.

Examples 6-9

Polymerization

The polymerizations were carried out at 40° C. under argon in a 1 l four-necked flask provided with contact thermometer, stirrer with Teflon blade, heating mantle and gas inlet tube. The appropriate amount of MAO (10% strength solution in toluene, for Cr:Al see Table 1) was added to a solution of the amount indicated in Table 1 of the appropriate complex in 250 ml of toluene and the mixture was heated to 40° C. on a water bath.

In the ethylene homopolymerizations, ethylene was passed through the solution at a flow rate of from about 20 to 40 l/h at atmospheric pressure. In the case of the ethylene/1-hexene copolymerization, 3 ml of hexene were placed in the flask shortly before the addition of ethylene and ethylene was subsequently passed through the mixture at a flow rate of from about 20 to 4/h at atmospheric pressure. The remainder of the hexene (10 ml) was added via a dropping funnel over a period of 15 minutes. After maintaining a constant ethylene flow for the time indicated in Table 1, the polymerization was stopped by addition of methanolic HCl solution (15 ml of concentrated hydrochloric acid in 50 ml of methanol). 250 ml of methanol were subsequently added and the white polymer formed was filtered off, washed with methanol and dried at 70° C.

Even in ethylene homopolymerizations, the catalysts of the present invention lead to ethylene polymers which are strongly branched and display low eta values.

We claim:
1. The monocyclopentadienyl complex comprising formula Cp-Z-A-M$^A$ (II), where:
Cp-Z-A is

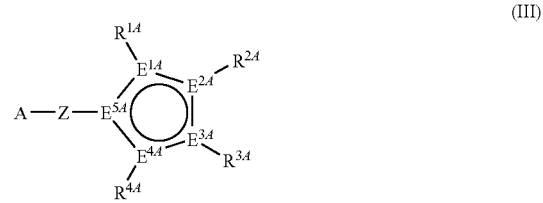

where:
$E^{1A}$-$E^{5A}$ are each carbon;
$R^{1A}$-$R^{4A}$ are each, independently of one another, hydrogen, a $C_1$-$C_{22}$-alkyl, a $C_2$-$C_{22}$-alkenyl, a $C_6$-$C_{22}$-aryl, an arylalkyl comprising from 1 to 10 carbon atoms in the alkyl part and 6-20 carbon atoms in the aryl part, or SiR$^{5A}_3$, where $R^{1A}$-$R^{4A}$ optionally can be substituted by at least one halogen and two vicinal $R^{1A}$-$R^{4A}$ optionally can be joined to form a five-, six- or seven-membered ring;
$R^{5A}$ are each, independently of one another, hydrogen, a $C_1$-$C_{20}$-alkyl, a $C_2$-$C_{20}$-alkenyl, a $C_6$-$C_{20}$-aryl, an arylalkyl comprising from 1 to 10 carbon atoms in the alkyl part and 6-20 carbon atoms in the aryl part, or two geminal $R^{5A}$ optionally can be joined to form a five- or six-membered ring;
Z is a divalent bridge between A and Cp and is

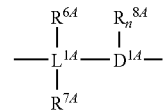

where
$L^{1A}$ is carbon, silicon or germanium;
$D^{1A}$ is an atom of group 15 or 16 of the Periodic Table of Elements;
n is 0 when $D^{1A}$ is an atom of group 16, and is 1 when $D^{1A}$ is an atom of group 15;
$R^{6A}$-$R^{8A}$ are each, independently of one another, hydrogen, a $C_1$-$C_{20}$-alkyl, a $C_2$-$C_{20}$-alkenyl, a $C_6$-$C_{20}$-aryl, an arylalkyl comprising from 1 to 10 carbon atoms in the alkyl part and 6-20 carbon atoms in the aryl part, or SiR$^{9A}_3$, where $R^{6A}$-$R^{8A}$ optionally can be substituted by at least one halogen and two geminal or

TABLE 1

| | | | | | | Polymerization results | | | | | |
|---|---|---|---|---|---|---|---|---|---|---|---|
| Ex. | Cat. From Ex. | Amount of cat. [mg] ([μmol]) | Cr:Al | t(poly) [min] | Hexene | Polymer [g] | Prod. [g/(mmol M · h)] | Eta value [dl/g] | Mw [g/mol] | Density [g/cm$^3$] | CH$_3$/1000 C. |
| 6 | 1 | 18.9 (47.8) | 1:500 | 60 | yes | 1.11 | 23 | 0.906 | 37443 | | |
| 7 | 3 | 11.2 (28.3) | 1:500 | 25 | no | 12.1 | 1025 | | | | |
| 8 | 4 | 10.2 (24.9) | 1:500 | 17 | no | 7.49 | 1064 | 0.974 | | 0.9468 | 12.8 |
| 9 | 5 | 5.56 (215) | 1:350 | 60 | no | 14.2 | 946 | 1.74 | | | | vicinal $R^{6A}$-$R^{8A}$ optionally can be joined to form a five- or six-membered ring;

$R^{9A}$ are each, independently of one another, hydrogen, a $C_1$-$C_{20}$-alkyl, a $C_2$-$C_{20}$-alkenyl, a $C_6$-$C_{20}$-aryl or an arylalkyl comprising from 1 to 10 carbon atoms in the alkyl part and 6-20 carbon atoms in the aryl part, a $C_1$-$C_{10}$-alkoxy or a $C_6$-$C_{10}$-aryloxy, or two $R^{9A}$ optionally can be joined to form a five- or six-membered ring;

A comprises formula (IV):

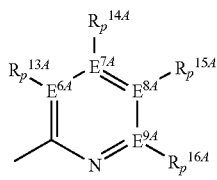

(IV)

where $E^{6A}$-$E^{9A}$ are each, independently of one another, carbon, or nitrogen;

$R^{13A}$-$R^{16A}$ are each, independently of one another, hydrogen, a $C_1$-$C_{20}$-alkyl, a $C_2$-$C_{20}$-alkenyl, a $C_6$-$C_{20}$-aryl, an arylalkyl comprising from 1 to 10 carbon atoms in the alkyl part and 6-20 carbon atoms in the aryl part, or $SiR^{17A}_3$, where $R^{13A}$-$R^{16A}$ optionally can be substituted by at least one halogen or nitrogen, or two vicinal $R^{13A}$-$R^{16A}$ or $R^{13A}$ and Z optionally can be joined to form a five- or six-membered ring;

$R^{17A}$ are each, independently of one another, hydrogen, a $C_1$-$C_{20}$-alkyl, a $C_2$-$C_{20}$-alkenyl, a $C_6$-$C_{20}$-aryl or an arylalkyl comprising from 1 to 10 carbon atoms in the alkyl part and 6-20 carbon atoms in the aryl part, or two $R^{17A}$ optionally can be joined to form a five- or six-membered ring;

p is 0 when $E^{6A}$-$E^{9A}$ is nitrogen, and is 1 when $E^{6A}$-$E^{9A}$ is carbon; and $M^A$ is chromium, molybdenum, or tungsten.

2. The monocyclopentadienyl complex as claimed in claim 1, wherein $L^{1A}$ is silicon.

3. The monocyclopentadienyl complex as claimed in claim 1, wherein $D^{1A}$ is oxygen, sulfur, nitrogen, or phosphorus.

4. The monocyclopentadienyl complex as claimed in claim 1, wherein -Z- is —$SiR^{6A}R^{7A}$—O—.

5. A catalyst system for olefin polymerization comprising:
A) at least one monocyclopentadienyl complex as claimed in claim 1;
B) optionally, an organic or inorganic support;
C) optionally, one or more activating compounds;
D) optionally, further catalysts suitable for olefin polymerization; and
E) optionally, one or more metal compounds comprising a metal of group 1, 2 or 13 of the Periodic Table of Elements.

6. A process for preparing polyolefins by polymerization or copolymerization olefins in presence of the catalyst system as claimed in claim 5.

* * * * *